United States Patent
Matsumoto et al.

(10) Patent No.: US 7,173,112 B2
(45) Date of Patent: Feb. 6, 2007

(54) ANTIBODY TO GALP AND USES THEREOF

(75) Inventors: Hirokazu Matsumoto, Ibaraki (JP); Yasuko Horikoshi, Ibaraki (JP); Chieko Kitada, Osaka (JP); Tetsuya Ohtaki, Ibaraki (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 83 days.

(21) Appl. No.: 10/490,917

(22) PCT Filed: Sep. 25, 2002

(86) PCT No.: PCT/JP02/09840

§ 371 (c)(1),
(2), (4) Date: Mar. 26, 2004

(87) PCT Pub. No.: WO03/027150

PCT Pub. Date: Apr. 3, 2003

(65) Prior Publication Data

US 2004/0214230 A1    Oct. 28, 2004

(30) Foreign Application Priority Data

Sep. 26, 2001    (JP) .............................. 2001-294528

(51) Int. Cl.
*C07K 16/00* (2006.01)
(52) U.S. Cl. .............................. 530/387.1; 424/130.1; 530/388.1
(58) Field of Classification Search .............. 536/387.1
See application file for complete search history.

(56) References Cited

U.S. PATENT DOCUMENTS

2004/0077531 A1* 4/2004 Matsumoto et al. ............ 514/8

FOREIGN PATENT DOCUMENTS

| CA | 2323503 A1 * | 3/1999 |
|---|---|---|
| EP | 1 065 214 A1 | 1/2001 |
| EP | 1 275 659 A1 | 1/2003 |
| JP | 2000-197483 | 7/2000 |
| JP | 2000-270871 | 10/2000 |
| WO | WO 01/27273 A1 | 4/2001 |
| WO | WO 01/77166 A1 | 10/2001 |

OTHER PUBLICATIONS

Fujiwara et al., "Immunocytochemical localization of galanin-like peptide (GALP) in pitulcytes of the rat posterior pituitary gland", Neuroscience Letters, 317(2):65-68 (2002).

Y. Takatsu et al., *Endocrinology*, vol. 142, No. 4, pp. 1626-1634, 2001.

T. Ohtaki et al., *Journ. of Bio. Chem.*, vol. 274, No. 52, pp. 37041-37045. 1999.

\* cited by examiner

*Primary Examiner*—Misook Yu
(74) *Attorney, Agent, or Firm*—David G. Conlin; Kathryn A. Piffat; Edwards Angell Palmer & Dodge, LLP

(57) ABSTRACT

The present invention intends to provide a novel monoclonal antibody having a binding specificity to GALP or its derivative, which is useful in developing therapeutic agents, preventive agents or diagnostic agent for diseases associated with GALP or its derivative, and a method of quantifying GALP using the antibody. More specifically, the present invention provides an antibody specifically reacting with a partial peptide in the C-terminal region of a polypeptide having the amino acid sequence represented by SEQ ID NO: 1, SEQ ID NO: 2 or SEQ ID NO: 3, or its derivative, and a method of quantifying GALP or its derivative.

8 Claims, 9 Drawing Sheets

ANTIBODY TO GALP AND USES THEREOF

CROSS-REFERENCES TO RELATED APPLICATIONS

The present application is a 35 U.S.C. §371 national stage of PCT application PCT/JP2002/009840, filed Sep. 25, 2002, which claims priority of Japanese Application 294528/2001, filed Sep. 26, 2001.

FIELD OF THE INVENTION

The present invention relates to an antibody having a binding specificity to a partial peptide in the C-terminal region of a polypeptide having the amino acid sequence represented by SEQ ID NO: 1, SEQ ID NO: 2 or SEQ ID NO: 3, or its derivative. More specifically, the present invention relates to an antibody, which is useful in developing a method of quantifying a polypeptide having the amino acid sequence represented by SEQ ID NO: 1, SEQ ID NO: 2 or SEQ ID NO: 3, or its derivative, in developing a diagnostic, preventive/therapeutic agent for diseases associated with the polypeptide having the amino acid sequence represented by SEQ ID NO: 1, SEQ ID NO: 2 or SEQ ID NO: 3, or its derivative.

BACKGROND ART

Various hormones and neurotransmitters regulate the biological functions via specific receptors present on cell membranes. Many of these receptor proteins are coupled with guanine nucleotide-binding protein (hereinafter simply referred to as G protein) and mediate the intracellular signal transduction via activation of G protein. As a peptide ligand to galanin receptor subtype 2 (GALR2), which is a G protein-coupled receptor, porcine ligand, human ligand and rat ligand were acquired (Published Japanese Patent Application KOKAI No. 2000-157273 and WO 99/48920). These ligands are sometime collectively referred to as galanin-like peptide (GALP) (J. Biol. Chem., 274, 37041, 1999). GALP shows a stronger affinity to GALR2 than galanin bound to a galanin receptor and from the receptor distribution, it is speculated that GALP would have a broad range of physiological activities. Further detailed studies on physiological significance of GALP are required.

It has been earnestly desired to develop an assay system for detection and quantification of GALP in a simple manner with high sensitivity.

DISCLOSURE OF THE INVENTION

The present invention intends to provide an antibody (preferably a monoclonal antibody), which can specifically quantify GALP or its derivative with high sensitivity, a method of detecting/quantifying GALP or its derivative using the antibody, and a diagnostic product using the same.

The present inventors have made extensive investigations to solve the foregoing problems and as a result, developed an immunoassay method, which involves using [$Cys^{43}$] rat GALP (43-560) as an immunogen, preparing a plurality of monoclonal antibodies, and using them in combination, and by which GALP or its derivative can be specifically detected with high sensitivity. That is, using the complex of keyhole limpet hemocyanin (hereinafter referred to as KLH) and [$Cys^{43}$] rat GALP (43-60) as an immunogen, monoclonal antibodies (e.g., GR-1Ca) capable of recognizing the C-terminal partial peptide of GALP or its derivative were obtained. These antibodies showed an extremely high affinity to GALP in the competitive immunoassay using peroxidase (HRP)-labeled [$Cys^{43}$] rat (43-60). Furthermore, it has also been found that a sandwich-immunoassay for GALP with extremely high sensitivity is provided by using this antibody in combination with the GR2-1Na antibody specifically reacting with a partial peptide in the N-terminal region of GALP or its derivative, which was already developed (Published Japanese Patent Application KOKAI No. 2000-157273). The present invention enables to assay GALP in a simple manner with high sensitivity, and greatly serves in clarifying the physiological functions of GALP or its derivative by determining changes in GALP in body fluids such as blood, cerebral fluid, urine, etc.

The present invention provides an antibody (preferably a monoclonal antibody), which specifically reacting with a partial peptide in the C-terminal region of GALP or its derivative; a hybridoma cell producing the monoclonal antibody; a method of producing the antibody and the hybridoma; a method of immunological assay for GALP or its derivative by the sandwich method, etc., in combination with the antibody (GR2-1Na) specifically reacting with a partial peptide in the N-terminal region of GALP or its derivative; and the like.

Thus, the present invention relates to the following features:

(1) An antibody specifically reacting with a partial peptide in the C-terminal region of a polypeptide having the amino acid sequence represented by SEQ ID NO: 1, SEQ ID NO: 2 or SEQ ID NO: 3, or its derivative;

(2) The antibody according to (1), wherein the partial peptide in the C-terminal region is a peptide having a 44–53 amino acid sequence in the amino acid sequence represented by SEQ ID NO: 1, SEQ ID NO: 2 or SEQ ID NO: 3;

(3) The antibody according to (1), wherein the partial peptide in the C-terminal region is a peptide having a 40–60, 41–60, 42–60, 43–60, 44–60, 45–60, 46–60, 47–60, 48–60, 49–60, 50–60, 44–54, 45–54, 46–54, 47–54, 48–54, 49–54 or 50–54 amino acid sequence in the amino acid sequence represented by SEQ ID NO: 1, SEQ ID NO: 2 or SEQ ID NO: 3;

(4) The antibody according to (1), which is labeled;

(5) The antibody according to (1), which is a monoclonal antibody;

(6) The monoclonal antibody according to (5), which is producible from a hybridoma cell shown by GR-1C (FERM BP-7682) and shown by GR-1Ca;

(7) A hybridoma cell according to (5), which produces the monoclonal antibody of (5);

(8) The hybridoma cell according to (7), which is shown by GR-1C (FERM BP-7682);

(9) A method of manufacturing the monoclonal antibody of (5), which comprises culturing the hybridoma cell of (7) in vivo or in vitro and collecting the monoclonal antibody of (5) from the body fluid or culture;

(10) A pharmaceutical comprising the antibody according to (1);

(11) A diagnostic product comprising the antibody according to (1);

(12) A method of quantifying a polypeptide having the amino acid sequence represented by SEQ ID NO: 1, SEQ ID NO: 2 or SEQ ID NO: 3, or its derivative, which comprises using the antibody according to (1);

(13) A method of quantifying a polypeptide having the amino acid sequence represented by SEQ ID NO: 1, SEQ ID NO: 2 or SEQ ID NO: 3, or its derivative in a sample fluid, which comprises using the antibody according to (1) and an antibody specifically reacting with a partial peptide in the N-terminal region of a polypeptide having the amino acid sequence represented by SEQ ID NO: 1, SEQ ID NO: 2 or SEQ ID NO: 3, or its derivative;

(14) A method of quantifying a polypeptide having the amino acid sequence represented by SEQ ID NO: 1, SEQ ID NO: 2 or SEQ ID NO: 3, or its derivative in a sample fluid, which comprises (1) reacting (i) the antibody according to (1) immobilized on a carrier with (ii) a labeled form of antibody specifically reacting with a partial peptide in the N-terminal region of a polypeptide having the amino acid sequence represented by SEQ ID NO: 1, SEQ ID NO: 2 or SEQ ID NO: 3, or its derivative and (iii) a sample fluid, or (2) reacting (i) an antibody specifically reacting with a partial peptide in the N-terminal region of a polypeptide having the amino acid sequence represented by SEQ ID NO: 1, SEQ ID NO: 2 or SEQ ID NO: 3, or its derivative, which is immobilized on a carrier, with (ii) a labeled form of the antibody according to (1) and (iii) a sample fluid, and then determining the activity of a marker on the immobilization carrier;

(15) The quantifying method according to (14), which comprises (1) reacting (i) the monoclonal antibody according to (6) immobilized on a carrier with (ii) a labeled form of monoclonal antibody shown by GR2-1Na, which is producible from a hybridoma cell shown by GR2-1N (FERM BP-6682) and (iii) a sample fluid, or (2) reacting (i) a monoclonal antibody shown by GR2-1N, which is producible from hybridoma cell shown by GR2-1N (FERM BP-6682), which is immobilized on a carrier with (ii) a labeled form of the antibody according to (6) and (iii) a sample fluid, and then determining the activity of a marker on the immobilization carrier;

(16) A method of quantifying a polypeptide having the amino acid sequence represented by SEQ ID NO: 1, SEQ ID NO: 2 or SEQ ID NO: 3, or its derivative in a sample fluid, which comprises competitively reacting the antibody according to (1), a sample fluid and a labeled form of the polypeptide having the amino acid sequence represented by SEQ ID NO: 1, SEQ ID NO: 2 or SEQ ID NO: 3, or its derivative, and determining a ratio of the labeled polypeptide having the amino acid sequence represented by SEQ ID NO: 1, SEQ ID NO: 2 or SEQ ID NO: 3 or its derivative, bound to the antibody;

(17) A method of diagnosing a disease associated with a polypeptide having the amino acid sequence represented by SEQ ID NO: 1, SEQ ID NO: 2 or SEQ ID NO: 3, or its derivative, which comprises using the antibody according to (1); and,

(18) A method of diagnosing obesity, sterility, collagen disease or rheumatic disease, which comprises using the antibody according to (1); and so on.

BEST MODE FOR CARRYING OUT THE INVENTION

Figure 1:
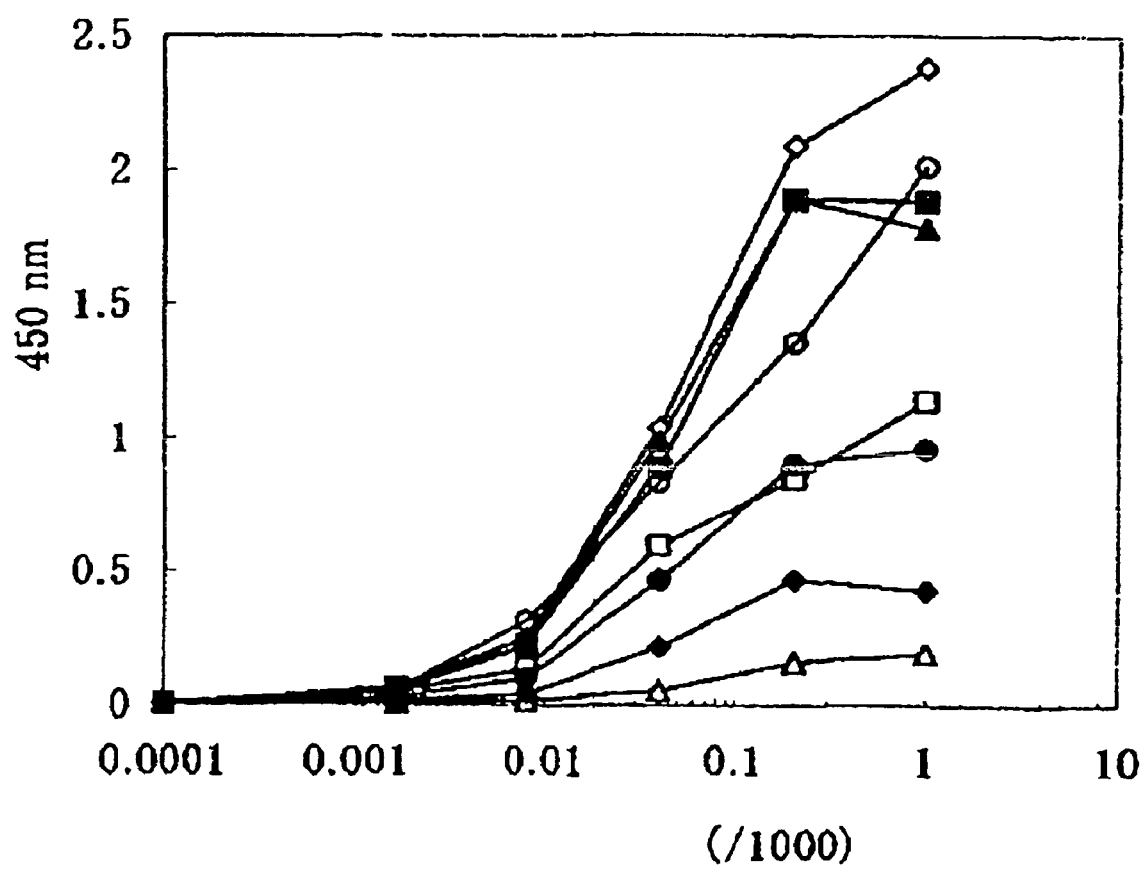
FIG. 1 shows the results of assay for antibody titer of mouse antisera immunized with the [$Cys^{43}$] rat GALP (43-60)-KLH complex as a function of dilution factor (per thousand) of antisera (X-axis).

Throughout the specification, the proteins (polypeptides) are represented in accordance with the conventional way of describing peptides, that is, the N-terminus (amino terminus) at the left hand and the C-terminus (carboxyl terminus) at the right hand. In the proteins used in the present invention including the polypeptide containing the amino acid sequence represented by SEQ ID NO: 1, SEQ ID NO: 2 or SEQ ID NO: 3, the C-terminus may be in any form of a carboxyl group, a carboxylate, an amide or an ester.

The polypeptide having the amino acid sequence represented by SEQ ID NO: 1, SEQ ID NO: 2 or SEQ ID NO: 3 (hereinafter sometimes referred to as GALP) includes a rat, human or porcine polypeptide, etc. consisting of 60 amino acid residues, and the like (hereinafter sometimes referred to as the peptide of the present invention).

The derivatives of GALP used in the present invention include, for example, those having the amino acid sequence represented by SEQ ID NO: 1, SEQ ID NO: 2 or SEQ ID NO: 3, wherein a part of amino acid residues are replaced by a replaceable group(s), the amino acid residues are in part deleted, the amino acid residues are in part added/inserted, etc.

Examples of the derivatives of polypeptide having the amino acid sequence represented by SEQ ID NO: 1, SEQ ID NO: 2 or SEQ ID NO: 3 are (i) those wherein at least 1 or 2 (preferably approximately 1 to 10, more preferably several (1 to 5) and most preferably 1, 2 or 3) amino acids are deleted of the amino acid sequence described above; (ii) those wherein at least 1 or 2 (preferably approximately 1 to 20 amino acids, more preferably approximately 1 to 10 amino acids, much more preferably several (1 to 5) and most preferably 1, 2 or 3) amino acids are added to the amino acid sequence described above; (iii) those wherein at least 1 or 2 (preferably approximately 1 to 20 amino acids, more preferably approximately 1 to 10 amino acids, much more preferably several (1 to 5) and most preferably 1, 2 or 3) amino acids are inserted into the amino acid sequence described above, or (iv) those wherein at least 1 or 2 (preferably approximately 1 to 10, more preferably several (1 to 5), and most preferably 1, 2 or 3) amino acids in the amino acid sequence described above are replaced with other amino acids.

As the partial peptide in the N-terminal region or the partial peptide in the C-terminal region of GALP or its derivatives used in the present invention, there are peptides having the amino acid sequence represented by SEQ ID NO: 1, SEQ ID NO: 2 or SEQ ID NO: 3, wherein a part of the amino acid residues are deleted, those wherein a part of the amino acid residues are replaced with replaceable groups (e.g., Cys, hydroxyl group, etc.), or those wherein a part of the amino acid residues are deleted and a part of he amino acid residues are replaced with replaceable groups (e.g., Cys, hydroxyl group, etc.), and the like.

Examples of partial peptides in the C-terminal region of GALP or its derivatives include GALP or its derivatives, of which approximately 42 to 54 residues are deleted in the N-terminal region of GALP or its derivatives.

More specifically, the partial peptides in the C-terminal region are the following polypeptides in the amino acid sequence represented by SEQ ID NO: 1, SEQ ID NO:2 or SEQ ID NO:3;
  (i) polypeptide having the 40–60 amino acid sequence,
  (ii) polypeptide having the 41–60 amino acid sequence,
  (iii) polypeptide having the 42–60 amino acid sequence,
  (iv) polypeptide having the 43–60 amino acid sequence,
  (v) polypeptide having the 44–60 amino acid sequence,
  (vi) polypeptide having the 45–60 amino acid sequence,
  (vii) polypeptide having the 46–60 amino acid sequence,
  (viii) polypeptide having the 47–60 amino acid sequence,
  (ix) polypeptide having the 48–60 amino acid sequence,
  (x) polypeptide having the 49–60 amino acid sequence,
  (xi) polypeptide having the 50–60 amino acid sequence,
  (xii) polypeptide having the 44–54 amino acid sequence,
  (xiii) polypeptide having the 45–54 amino acid sequence,
  (xiv) polypeptide having the 46–54 amino acid sequence,
  (xv) polypeptide having the 47–54 amino acid sequence,
  (xvi) polypeptide having the 48–54 amino acid sequence,
  (xvii) polypeptide having the 49–54 amino acid sequence,
  (xviii) polypeptide having the 50–54 amino acid sequence, and
  (xix) those wherein a part of amino acid residues (e.g., 1 residue) are replaced with replaceable groups in these polypeptides; and so on.

Examples of the partial peptides in the N-terminal region of GALP or its derivatives are those deleted of approximately 40 to 50 residues in the N-terminal region of GALP or its derivatives.

The partial peptides in the N-terminal region include the following polypeptides in the amino acid sequence represented by SEQ ID NO: 1, SEQ ID NO: 2 or SEQ ID NO: 3;
  (i) polypeptide having the 1–4 amino acid sequence,
  (ii) polypeptide having the 1–5 amino acid sequence,
  (iii) polypeptide having the 1–6 amino acid sequence,
  (iv) polypeptide having the 1–7 amino acid sequence,
  (v) polypeptide having the 1–8 amino acid sequence,
  (vi) polypeptide having the 1–9 amino acid sequence, and
  (vii) those wherein a part of amino acid residues (e.g., 1 residue) in these polypeptides are replaced with replaceable groups; and so on.

The antibodies of the present invention, which specifically react with the partial peptides in the C-terminal region of GALP or its derivatives, may be any antibody so long as they specifically react with partial peptides in the C-terminal region of GALP or its derivatives (preferably partial peptides in the C-terminal region of the peptide represented by SEQ ID NO:2). These antibodies include antibodies specifically reacting with the following polypeptides in the amino acid sequence represented by SEQ ID NO: 1, SEQ ID NO:2 or SEQ ID NO:3: (i) a polypeptide having the 40–60 amino acid sequence, (ii) a polypeptide having the 41–60 amino acid sequence, (iii) polypeptide having the 42–60 amino acid sequence, (iv) polypeptide having the 43–60 amino acid sequence, (v) polypeptide having the 44–60 amino acid sequence, (vi) polypeptide having the 45–60 amino acid sequence, (vii) polypeptide having the 46–60 amino acid sequence, (viii) polypeptide having the 47–60 amino acid sequence, (ix) polypeptide having the 48–60 amino acid sequence, (x) polypeptide having the 49–60 amino acid sequence, (xi) polypeptide having the 50–60 amino acid sequence, (xii) polypeptide having the 44–54 amino acid sequence, (xiii) polypeptide having the 45–54 amino acid sequence, (xiv) polypeptide having the 46–54 amino acid sequence, (xv) polypeptide having the 47–54 amino acid sequence, (xvi) polypeptide having the 48–54 amino acid sequence, (xvii) polypeptide having the 49–54 amino acid sequence, (xviii) polypeptide having the 50–54 amino acid sequence, and (xix) polypeptide wherein a part of amino acid residues (e.g., 1 residue) in these polypeptides are replaced with replaceable groups; etc.

As the antibody of the present invention, which specifically reacts with the partial peptides in the C-terminal region of GALP or its derivative, a monoclonal antibody is preferred. More specifically, the antibody of the present invention, which specifically reacts with the partial peptide in the C-terminal region of GALP or its derivatives, includes an antibody specifically reacting with [$Cys^{43}$] rat GALP (43-60), etc. [$Cys^{43}$] rat GALP (43-60) is a 43–60 amino acid sequence in the amino acid sequence represented by SEQ ID NO: 1 and means a polypeptide wherein Cys is replaced for the 43rd residue in this amino acid sequence. More preferred antibodies are antibodies which specifically react with the partial peptides in the C-terminal region of GALP or its derivatives but do not react with the partial peptides in the N-terminal region.

An example of the antibody of the present invention, which specifically reacts with the partial peptides in the C-terminal region of GALP or its derivatives, includes the monoclonal antibody shown by GR-1Ca producible from the hybridoma shown by GR-1C (FERM BP-7682).

As such, the antibody of the present invention, which specifically reacts with the partial peptides in the C-terminal region of GALP or its derivatives, can react with GALP or its derivatives by recognizing a particular amino acid sequence in the C-terminal region of GALP or its derivatives.

The antibodies of the present invention, which specifically react with the partial peptides in the N-terminal region of GALP or its derivatives, may be any antibody so long as they specifically react with partial peptides in the N-terminal region of GALP or its derivatives. These antibodies include antibodies specifically reacting with the following polypeptides in the amino acid sequence represented by SEQ ID NO: 1, SEQ ID NO: 2 or SEQ ID NO: 3: (i) polypeptide having the 1–4 amino acid sequence, (ii) polypeptide having the 1–5 amino acid sequence, (iii) polypeptide having the 1–6 amino acid sequence, (iv) polypeptide having the 1–7 amino acid sequence, (v) polypeptide having the 1–8 amino acid sequence, (vi) polypeptide having the 1–9 amino acid sequence, and (vii) a polypeptide wherein a part of amino acid residues (e.g., 1 residue) in these polypeptides are replaced with replaceable groups. Preferred antibodies specifically reacting with the partial peptides in the N-terminal region of GALP or its derivatives are monoclonal antibodies.

More specifically, the antibodies include those specifically reacting with rat GALP (1–9) (polypeptide having the 1–9 amino acid sequence in the amino acid sequence represented by SEQ ID NO:1). Among them, more preferred are such antibodies that specifically react with the partial peptides in the N-terminal region but do not react with the partial peptides in the C-terminal region. An example of the antibodies specifically reacting with the partial peptides in the N-terminal region includes monoclonal antibody shown by GR2-1Na producible from the hybridoma cell shown by GR2-1N (FERM BP-6682) (Published Japanese Patent Application KOKAI No. 2000-157273).

As such, the antibody, which specifically reacts with the partial peptides in the N-terminal region of GALP or its derivatives, can react with GALP or its derivatives by recognizing a particular amino acid sequence in the N-terminal region of GALP or its derivatives.

Hereinafter, explanation is given to methods of preparing antigens of the antibodies specifically reacting with the partial peptides in the C-terminal region of GALP or its derivatives (hereinafter sometimes referred to as the antibody of the present invention) and methods of manufacturing the antibodies.

(1) Preparation of Antigen

To prepare the antibody of the present invention, any antigen such as GALP or its derivatives, synthetic peptides having 1 or 2 more antigenic determinants, which are the same as in GALP, etc., may be used (hereinafter these antigens are sometimes collectively referred to as the GALP antigen).

GALP or its derivatives can be (a) prepared from mammalian tissue or cells of human, monkey, rat, mouse, swine, etc. by publicly known methods or with modifications, (b) chemically synthesized by publicly known peptide synthesis methods using a peptide synthesizer, etc., or (c) manufactured by culturing a transformant bearing a DNA encoding GALP or its derivatives.

(a) Where the GALP antigen is prepared from the mammalian tissues or cells, the tissues or cells are homogenized, then extracted with an acid, an alcohol, etc., and the extract is purified and isolated by a combination of salting-out, dialysis, gel filtration, chromatography techniques such as reverse phase chromatography, ion exchange chromatography, affinity chromatography and the like. Thus, the GALP antigen can be prepared.

(b) Synthetic peptides used when the GALP antigen is chemically synthesized are, for example, a peptide having the same structure as that of the GALP antigen purified from natural one, a peptide containing 1 or 2 more amino acid sequences, which are the same amino acid sequences consisting of at least 3, preferably at least 6 amino acids in an optional region of the amino acid sequence of GALP, etc.

(c) Where the GALP or its derivatives are manufactured using the DNA-bearing transformants, the DNA can be produced in accordance with publicly known cloning techniques (e.g., the method described in Molecular Cloning (2nd ed., J. Sambrook et al., Cold Spring Harbor Lab. Press, 1989), etc.). The cloning techniques include (1) a method in which transformants containing DNAs encoding the GALP or its derivatives are obtained from cDNA library by hybridization using DNA probes or DNA primers designed based on the amino acid sequence of GALP or its derivatives, or (2) a method in which transformants containing DNAs encoding the GALP or its derivatives are obtained by PCR using DNA primers designed based on the amino acid sequence of GALP or its derivatives, etc.

Peptides used as the GALP antigen can be prepared (1) by peptide synthesis methods publicly known, or (2) by cleaving peptides having the amino acid sequence represented by SEQ ID NO: 1, SEQ ID NO:2 or SEQ ID NO:3 with an appropriate peptidase.

For the methods for peptide synthesis, for example, any of solid phase synthesis and liquid phase syntheses may be used. That is, the partial peptides or amino acids that can construct the peptide are condensed with the remaining part. Where the product contains protecting groups, these protecting groups are removed to give the desired peptide. By the condensation or removal of the protecting groups, objective peptides can be prepared. Publicly known methods for condensation and removal of the protecting groups are methods described in (i) or (ii) below.

(i) M. Bodanszky & M. A. Ondetti: Peptide Synthesis, Interscience Publishers, New York (1966)

(ii) Schroeder & Luebke: The Peptide, Academic Press, New York (1965)

After the reaction, the product may be purified and isolated by a combination of conventional purification methods such as solvent extraction, distillation, column chromatography, liquid chromatography, recrystallization, etc. to give the peptide. When the peptide obtained by the above methods is in a free form, the peptide can be converted into an appropriate salt by a publicly known method; when the peptide is obtained in a salt form, it can be converted into a free form by a publicly known method.

Amides of the peptide may be obtained using commercially available resins for peptide synthesis, which are suitable for formation of the amides. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmehtylphenyl acetamidomethyl resin, polyacrylamide resin, 4-(2',4'-dimethoxyphenylhydroxymethyl)phenoxy resin, 4-(2',4'-dimethoxyphenyl-Fmoc-aminoethyl) phenoxy resin, etc. Using these resins, amino acids in which α-amino groups and functional groups on the side chains are appropriately protected are condensed on the resin in the order of the sequence of the objective peptide according to various condensation methods publicly known in the art. At the end of the reaction, the peptide is cut out from the resin and at the same time, the protecting groups are removed to obtain the objective peptide. Alternatively, the objective peptide may also be obtained by protecting the peptide in part with chlorotrityl resin, oxime resin, 4-hydroxybenzoic acid type resin, etc., and removing the protective groups from the taken out peptide in a conventional manner.

For condensation of the protected amino acids described above, a variety of activation reagents for peptide synthesis may be used, and carbodimides are particularly preferable. Examples of such carbodiimides include DCC, N,N'-diisopropylcarbodiimide, N-ethyl-N'-(3-dimethylaminoprolyl) carbodiimide, etc. For activation by these reagents, the protected amino acids in combination with a racemization inhibitor (e.g., HOBt, HOOBt) are added directly to the resin, or the amino acids previously protected in the form of symmetric acid anhydrides, HOBt esters or HOOBt esters are activated, followed by adding the thus activated protected amino acids to the resin. Solvents suitable for use to activate the protected amino acids or condense with the resin may be appropriately chosen from solvents known to be usable for peptide condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; tertiary amines such as pyridine, etc.; ethers such as dioxane, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to peptide bond-forming reactions and is usually selected in the range of approximately −20° C. to 50° C. The activated amino acid derivatives are used generally in an excess of about 1.5 to about 4 times. The condensation is examined by a test using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to cancel adverse effects on the subsequent reactions.

Examples of the protecting groups used to protect the amino groups of the starting compounds include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc. Examples of the protecting groups of a carboxyl group include, in addition to a $C_{1-6}$ alkyl group, a $C_{3-8}$ cycloalkyl group and a $C_{7-14}$ aralkyl group, 2-adamantyl, 4-nitrobenzyl, 4-methoxybenzyl, 4-chlorobenzyl, phenacyl and benzyloxycarbonyl hydrazide, t-butoxycarbonyl hydrazide, trityl hydrazide and the like.

The hydroxyl group of serine and threonine can be protected through, for example, its esterification or etherification. Examples of the groups appropriately used for the esterification include a lower ($C_{1-6}$) alkanoyl group, such as acetyl group, etc.; an aroyl group such as benzoyl group, etc., and a group derived from carbonic acid such as benzyloxycarbonyl group, ethoxycarbonyl group, etc. Examples of a group suitable for the etherification include benzyl group, tetrahydropyranyl group, t-butyl group, etc.

Examples of groups for protecting the phenolic hydroxyl group of tyrosine include Bzl, ClBzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, Bom, Bum, Boc, Trt, Fmoc, etc.

Examples of the activated carboxyl groups in the starting compounds include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)]. As the activated amino acids, in which the amino groups are activated in the starting material, the corresponding phosphoric amides are employed.

To eliminate (split off) the protecting groups, there are used catalytic reduction under hydrogen gas flow in the presence of a catalyst such as Pd-black, Pd-carbon, etc.; an acid treatment with anhydrous hydrofluoric acid, methanesulfonic acid, trifluoromethane-sulfonic acid or trifluoroacetic acid, or a mixture solution of these acids; a treatment with a base such as diisopropylethylamine, triethylamine, piperidine, piperazine, etc.; and reduction with sodium in liquid ammonia; or the like. The elimination of the protecting groups by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol, 1,2-ethanedithiol, etc. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of the functional groups that should not be involved in the reaction of the starting materials, protecting groups, elimination of the protecting groups and activation of the functional groups involved in the reaction may be appropriately selected from publicly known groups and publicly known means.

In another method for obtaining the amides of the peptide, for example, the α-carboxyl group of the carboxy terminal amino acid is first protected by amidation; the peptide chain is then extended to a desired length toward the amino group side. Thereafter, a peptide in which only the protecting group of the N-terminal α-amino group in the peptide chain has been eliminated from the peptide and a peptide (or amino acids) in which only the protecting group of the C-terminal carboxyl group has been eliminated are prepared. The two peptides are condensed in a mixture of the solvents described above. The details of the condensation reaction are the same as described above. After the protected peptide obtained by the condensation is purified, all the protecting groups are eliminated by the method described above to give the desired crude peptide. This crude peptide is purified by various known purification means. Lyophilization of the major fraction gives the amide of the desired peptide.

To prepare the esterified peptide, for example, the α-carboxyl group of the carboxy terminal amino acid is condensed with a desired alcohol to prepare the amino acid ester, which is followed by procedure similar to the preparation of the amidated peptide above to give the ester form of the desired peptide.

The GALP antigen may be provided for direct immunization in its immobilized form. The GALP antigen may also be bound or adsorbed to an appropriate carrier and the complex produced may be provided for immunization. A mixing ratio of the carrier to the GALP antigen (hapten) may be in any ratio of any type, as long as the antibody can be efficiently produced to the GALP antigen. A high molecular carrier conventionally used to produce an antibody to a hapten may be used in a weight ratio of 0.1 to 100 based on 1 of hapten. As such a high molecular carrier, there are used a naturally occurring high molecular carrier and a synthetic high molecular carrier. Examples of the naturally occurring high molecular carrier used are serum albumin from mammals such as bovine, rabbit, human, etc., thyroglobulins from mammals such as bovine, rabbit, etc., hemoglobins from mammals such as bovine, rabbit, human, sheep, etc or KHL hemocyanin.

As the synthetic high molecular carrier, there may be used, for example, a variety of latexes including polymers or copolymers, etc., such as polyamino acids, polystyrenes, polyacryls, polyvinyls, polypropylenes, etc.

For coupling of the hapten and the carrier, a variety of condensing agents can be used. Examples of the condensing agents, which are advantageously employed, are diazonium compounds such as bis-diazotized benzidine through crosslinking of tyrosine, histidine or tryptophan; dialdehyde compounds such as glutaraldehyde, etc. through crosslinking of amino groups therebetween; diisocyanate compounds such as toluene-2,4-diisocyanate, etc.; dimaleimide compounds such as N,N'-o-phenylenedimaleimide, etc. by crosslinking of thiols therebetween; maleimide activated ester compounds by crosslinking of an amino group with a thiol group; carbodiimide compounds by crosslinking of an amino group with a carboxyl group; etc. In the crosslinking of amino groups with each other, one amino group is reacted with an activated ester reagent (e.g., SPDP, etc.) having dithiopyridyl and then reduced to introduce the thiol group, whereas another amino group is introduced with a maleimide group using a maleimide activated ester reagent, and the two groups may be reacted with each other.

(2) Preparation of Monoclonal Antibody

The GALP antigen is administered to warm-blooded animal either solely or together with carriers or diluents to the site where the production of antibody is possible by administration routes such as intraperitoneally, intravenously, subcutaneously, etc. In order to potentiate the antibody productivity upon the administration, complete Freund's adjuvants or incomplete Freund's adjuvants may be administered. The administration is usually carried out once in every 2 to 6 weeks and approximately 2 to 10 times in total. Examples of the warm-blooded animal are monkeys, rabbits, dogs, guinea pigs, mice, rats, sheep, goats, chicken, etc. with mice being preferred for the preparation of monoclonal antibodies.

In the preparation of monoclonal antibodies, from warm-blooded animals, e.g., mice, immunized with the GALP antigen, the animal wherein the antibody titer is noted is selected, then the spleen or lymph node is collected after 2 to 5 days from the final immunization and antibody-producing cells contained therein are fused with myeloma cells to give anti-GALP monoclonal antibody-producing hybridomas. Measurement of the anti-GALP antibody titer in antisera may be made, for example, by reacting a labeled form of GALP, which will be described later, with the antiserum followed by assaying the binding activity of a marker bound to the antibody. The fusion may be operated, for example, by the known Kohler and Milstein method [Nature, 256, 495 (1975)]. Examples of fusion accelerators are polyethylene glycol (PEG), Sendai virus, etc., of which PEG is preferably employed. Examples of the myeloma cells are NS-1, P3U1, SP2/0, AP-1, etc. In particular, P3U1 or the like is preferably employed. A preferred ratio in count of the antibody-producing cells (spleen cells) to the myeloma cells used is within a range of approximately 1:1 to 20:1. When PEG (preferably, PEG 1000 to PEG 6000) is added in a concentration of approximately 10 to 80% followed by incubation generally at 20 to 40° C., preferably at 30 to 37° C. generally for 1 to 10 minutes, an efficient cell fusion can be carried out.

Various methods can be used for screening of the anti-GALP antibody-producing hybridomas. Examples of such methods include a method which comprises adding the hybridoma supernatant to a solid phase (e.g., microplate) adsorbed with GALP or its derivatives, or partial peptides thereof directly or together with a carrier, then adding an anti-immunoglobulin antibody (when mouse cells are used for the cell fusion, anti-mouse immunoglobulin antibody is used) labeled with a radioactive substance, an enzyme or the like, or Protein A and detecting the anti-GALP monoclonal antibody bound to the solid phase; a method which comprises adding the hybridoma supernatant to a solid phase adsorbed with an anti-immunoglobulin antibody or Protein A, adding GALP labeled with a radioactive substance, an enzyme, etc. and detecting the GALP monoclonal antibodies bound to the solid phase; etc. Screening and plating of the anti-GALP monoclonal antibodies can be performed generally in a medium for animal cells (e.g., RPMI 1640) containing 10–20% fetal calf serum and supplemented with HAT (hypoxanthine, aminopterin and thymidine). The antibody titer in the hybridomas culture supernatant can be assayed as in the assay for the antibody titer in the antisera described above.

Separation and purification of the anti-GALP monoclonal antibody can be carried out by methods applied to conventional separation and purification of immunoglobulins, as in the conventional methods for separation and purification of polyclonal antibodies (e.g., salting-out, alcohol precipitation, isoelectric point precipitation, electrophoresis, adsorption and desorption with ion exchangers (e.g., DEAE), ultracentrifugation, gel filtration, or a specific purification method which involves collecting only an antibody with an activated adsorbent such as a GALP antigen-binding solid phase, Protein A, Protein G, etc. and dissociating the binding to obtain the antibody and the like).

As described above, the antibody of the present invention can be produced by culturing hybridoma cells in a warm-blooded animal in vivo or in vitro and collecting the antibody from the body fluids or culture.

The antibody specifically reacting with the partial peptides in the N-terminal region of GALP or its derivatives can be produced in a similar manner to the methods described above; alternatively, the antibody can also be produced by publicly known methods, e.g., by the method described in Published Japanese Patent Application KOKAI No. 2000-157273.

The antibody of the present invention can quantify efficiently human GALP, rat GALP and porcine GALP or derivatives thereof.

Hereinafter, applications of the antibody of the present invention including the method of quantifying GALP or its derivatives (immunoassay), etc. are described in detail.

(1) Method of Quantifying GALP or its Derivatives

Using the antibody of the present invention, GALP can be assayed and also detected by tissue staining, or the like. For these purposes, the antibody molecule itself may be used, or F(ab')$_2$, Fab' or Fab fractions of the antibody molecule may be used.

The quantification method using the antibody of the present invention is not particularly limited. Any quantification method can be used, so long as the amount of antibody, antigen or antibody-antigen complex corresponding to the amount of antigen (e.g., the amount of GALP) in a fluid to be tested can be detected by chemical or physical means and the amount of the antigen can be calculated from a standard curve prepared from standard solutions containing known amounts of the antigen.

For such an assay method, for example, the sandwich method, the competitive method, the immunometric method, nephrometry, etc. are used, and the sandwich method and the competitive method described below are more preferred in terms of sensitivity and specificity, with the sandwich method being particularly preferable.

(1) Sandwich Method

The sandwich method is a quantification method, in which the antibody of the present invention immobilized on a carrier is reacted with a labeled form of the antibody of the present invention and a sample fluid, and the activity of a marker is assayed to quantify GALP or its derivative in the sample fluid.

Preferably, the sandwich method includes:
(i) A method for quantification of GALP or its derivative in a sample fluid, which comprises reacting the antibody specifically reacting with a partial peptide in the N-terminal region of GALP or its derivative immobilized onto a carrier, a labeled form of the antibody specifically reacting with a partial peptide in the C-terminal region and the sample fluid, and assaying the activity of a marker;

(ii) A method for quantification of GALP or its derivative in a sample fluid, which comprises reacting the antibody specifically reacting with a partial peptide in the C-terminal region of GALP or its derivative immobilized onto a carrier, a labeled form of the antibody specifically reacting with a partial peptide in the N-terminal region and the sample fluid, and assaying the activity of a marker; etc.

A more preferred technique of the sandwich method includes (iii) the method for quantification of (i) or (ii), wherein the antibody specifically reacting with a partial peptide in the N-terminal region of GALP or its derivative is a monoclonal antibody shown by GR2-1Na, and the antibody specifically reacting with a partial peptide in the C-terminal region of GALP or its derivative is a monoclonal antibody shown by GR-1Ca.

In the sandwich method, a sample fluid is reacted with the immobilized antibody specifically reacting with a partial peptide in the C-terminal region of GALP or its derivative, or the antibody specifically reacting with a partial peptide in the N-terminal region of GALP or its derivative (primary reaction) and then with a labeled form of the antibody specifically reacting with a partial peptide in the C-terminal region of GALP or its derivative, or the antibody specifically reacting with a partial peptide in the N-terminal region of GALP or its derivative (secondary reaction), and the activity of a labeling agent on the immobilizing carrier is measured, whereby the amount of GALP in the sample fluid can be quantified. The order of the primary and secondary reactions may be performed simultaneously or at time intervals. The labeling agent and methods of immobilization may be based on those described above. In the immunoassay by the sandwich method, the antibodies used for solid phase or antibodies for labeling are not necessarily one species, but a mixture of two or more species of antibodies may be used for purposes of increasing the measurement sensitivity, etc. In the method of assaying GALP by the sandwich method, for example, when the antibodies used in the primary reaction recognize the partial peptides in the C-terminal region of GALP or its derivatives, the antibodies used in the secondary reaction, antibodies are preferably those recognizing partial peptides other than the C-terminal region (i.e., the N-terminal region). When the antibodies used for the primary reaction recognize partial peptides in the N-terminal region of GALP or its derivatives, the antibodies used in the secondary reaction, antibodies recognizing partial peptides other than the N-terminal region (i.e., the C-terminal region) are preferably employed.

As specific examples of such antibodies, there are used a monoclonal antibody prepared using [$Cys^{43}$] rat GALP (43–60) as an immunogen and a monoclonal antibody prepared using GALP (1–9) as an immunogen. These antibodies are preferably used in the form labeled with horse radish peroxidase (HRP).

(2) Competitive Method

In the competitive method, GALP or its derivative is quantified by competitively reacting the antibody of the present invention, a sample fluid and a labeled form of GLP or its derivative, and measuring a ratio of the labeled form of GALP or its derivative bound to the antibody.

Preferably, quantification of GALP or its derivative in a sample fluid by the competitive method is carried out using, e.g., solid phase technique.

Specifically, anti-mouse IgG antibody (manufactured by ICN/CAPPEL) is used as an antibody for solid phase, (i) the antibody of the present invention (e.g., GR-1Ca), (ii) the peptide represented by SEQ ID NO: 2 or SEQ ID NO: 3, which is labeled with HRP and (iii) a sample fluid are added to a plate where the antibody for solid phase is present; after the reaction, the HRP activity adsorbed onto the solid phase is assayed to quantify the GALP or its derivative.

(3) Immunometry

In the immunometry, an antigen in a sample fluid and an antigen immobilized to a solid phase are competitively reacted with a given amount of a labeled form of the antibody of the present invention, followed by separating the solid phase from the liquid phase; or the antigen in a sample fluid is reacted with an excess amount of a labeled form of the antibody of the present invention, then an antigen immobilized to a solid phase is added to bind a labeled form of the unreacted antibody of the present invention to the solid phase, followed by separating the solid phase from the liquid phase. Next, the quantity of a marker in any of the phases is measured to determine the amount of the antigen in the sample fluid.

(4) Nephrometry

In the nephrometry, the amount of insoluble sediment, which is produced as a result of the antigen-antibody reaction in a gel or in a solution, is measured. When the amount of an antigen in a sample fluid is small and only a small amount of the sediment is obtained, laser nephrometry utilizing laser scattering can be suitably used.

In the quantification methods (1) through (4) described above, labeling agents used for the assay method using labeling substances are not particularly limited but radioisotopes, enzymes, fluorescent substances, luminescent substances, etc. are employed. Preferred examples of the radioisotopes include, but are not limited thereto, [$^{125}$I], [$^{131}$I], [$^{3}$H], [$^{14}$C], etc. The enzymes described above are not particularly limited but are preferably enzymes which are stable and have a high specific activity, and include β-galactosidase, β-glucosidase, an alkaline phosphatase, a peroxidase, malate dehydrogenase, etc. The fluorescent substances are not particularly limited but examples include fluorescamine, fluorescein isothiocyanate, etc. The luminescent substances described above are not particularly limited but examples include luminol, a luminol derivative, luciferin, lucigenin, etc. Furthermore, the biotin-avidin system may be used as well for binding of an antibody to a labeling agent.

For immobilization of antigen or antibody, physical adsorption may be used. Chemical binding techniques conventionally used for insolubilization or immobilization of proteins, enzymes, etc. may also be used. For carriers, there are used, e.g., insoluble polysaccharides such as agarose, dextran, cellulose, etc.; synthetic resin such as polystyrene, polyacrylamide, silicon, etc., and glass or the like.

In applying each of these immunoassays to the method of the present invention, it is not necessary to set any special condition, operation, etc. The assay system for GALP or its derivatives may be constructed in addition to the conditions or operations conventionally used for each of the methods, taking into account the technical consideration of one skilled in the art. For the details of such conventional technical means, reference may be made to a variety of reviews, reference books, etc. (for example, Hiroshi Irie (ed.): "Radioimmunoassay" (published by Kodansha, 1974)]; Hiroshi Irie (ed.): "Radioimmunoassay; Second Series" (published by Kodansha, 1979); Eiji Ishikawa, et al. (ed.):

"Enzyme Immunoassay" (published by Igaku Shoin, 1978); Eiji Ishikawa, et al. (ed.): "Enzyme Immunoassay" (Second Edition) (published by Igaku Shoin, 1982); Eiji Ishikawa, et al. (ed.): "Enzyme Immunoassay" (Third Edition) (published by Igaku Shoin, 1987); "Methods in Enzymology" Vol. 70 (Immunochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies)) (all published by Academic Press); etc.). Thus, the antibody of the present invention enables to quantify GALP or its derivatives with high sensitivity and is useful for clarification of the physiological functions of GALP and for the prevention/treatment or diagnosis of diseases/symptoms associated with GALP.

GALP has a specific blood LH level increasing activity (LH secretion promoting activity), and its reactivity increases in Zucker fatty rats, in which abnormality is found in the leptin receptor.

By determining the level of GALP or its derivatives contained in body fluids (blood, plasma, serum, urine, etc.) using the antibody of the present invention, a diagnosis can be made for diseases associated with GALP or its derivatives [for example, insufficient LH secretion-related diseases (e.g., obesity, sterility, irregular menstruation, dysmenorrhea, amenorrhea, premenstrual syndrome, menopausal symptoms, dyspituitarism, etc.), LH oversecretion-related disorders (e.g., prostate cancer, prostatic hyperplasia, endometriosis, precocious puberty, ovarian cancer, LH-producing pituitary tumor, etc.), dementia, diabetes, immune disorders [e.g., collagen diseases (e.g., systemic lupus erythematosus, scleroderma (systemic scleroderma), dermatomyositis, chronic articular rheumatism, rheumatic fever, periarteritis nodosa, etc.), rheumatic disorders (e.g., arthritis deformans, traumatic arthritis, gout, pseudogout, ulcerative colitis, hemophilia), inflammation, myasthenia gravis, glomerulonephritis, multiple sclerosis, Sjögren's syndrome, insulin-resistant diabetes, etc.], abnormalities in water-electrolyte metabolism (e.g., pollakiuria, hyponatremia, hypernatremia, hypokalemia, hyperkalemia, metabolic alkalosis, etc.) or the like] and so on. In addition, the antibody of the present invention can be used to detect GALP or its derivatives present in sample fluids such as body fluids, tissues, etc. Moreover, the antibody of the present invention is available for preparation of antibody columns used to purify GALP or its derivatives, detection of GALP or its derivatives in each fraction upon purification, analysis of the behavior of GALP or its derivatives in cells to be tested; etc.

(2) Pharmaceutical Comprising the Antibody of the Present Invention

As described above, the antibody of the present invention can be used as a pharmaceutical such as preventive/therapeutic agent or diagnostic product of diseases associated with GALP or its derivatives [for example, insufficient LH secretion-related diseases (e.g., obesity, sterility, irregular menstruation, dysmenorrhea, amenorrhea, premenstrual syndrome, menopausal symptoms, dyspituitarism, etc.), overexpression-related disorders (e.g., prostate cancer, prostatic hyperplasia, endometriosis, precocious puberty, ovarian cancer, LH-producing pituitary tumor, etc.), dementia, diabetes, immune disorders [e.g., collagen diseases (e.g., systemic lupus erythematosus, scleroderma (systemic scleroderma), dermatomyositis, chronic articular rheumatism, rheumatic fever, periarteritis nodosa, etc.), rheumatic disorders (e.g., arthritis deformans, traumatic arthritis, gout, pseudogout, ulcerative colitis, hemophilia), inflammation, myasthenia gravis, glomerulonephritis, multiple sclerosis, Sjögren's syndrome, insulin-resistant diabetes, etc.], abnormalities in water-electrolyte metabolism (e.g., pollakiuria, hyponatremia, hypernatremia, hypokalemia, hyperkalemia, metabolic alkalosis, etc.) or the like] and so on.

The preventive/therapeutic agent comprising the antibody of the present invention is safe and low toxic, and can be administered parenterally or orally to human or mammals (e.g., rats, rabbits, sheep, swine, bovine, cats, dogs, monkeys, etc.) as it is in the form of liquid preparations or as a pharmaceutical composition of appropriate dosage form.

The antibody of the present invention may be administered in its intact form or in the form of an appropriate pharmaceutical composition. The pharmaceutical composition used for administration may contain the antibody of the present invention or its salt, a pharmacologically acceptable carrier and a diluent or an excipient. Such a pharmaceutical composition is provided in a dosage form suitable for oral or parenteral administration.

Examples of the composition for parenteral administration are injectable preparations, suppositories, etc. The injectable preparations may include dosage forms such as intravenous, subcutaneous, intracutaneous and intramuscular injections, drip infusions, etc. These injectable preparations may be prepared by methods publicly known. For example, the injectable preparations may be prepared by dissolving, suspending or emulsifying the antibody of the present invention or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate dissolution aid such as an alcohol (e.g., ethanol), a polyalcohol (e.g., propylene glycol, polyethylene glycol), a nonionic surfactant (e.g., polysorbate 80, HCO-50 (polyoxyethylene (50 mols) adduct of hydrogenated castor oil)), etc. As the oily medium, there are employed, e.g., sesame oil, soybean oil, etc., which may be used in combination with a dissolution aid such as benzyl benzoate, benzyl alcohol, etc. The injection thus prepared is preferably filled in an appropriate ampoule. The suppository used for rectal administration may be prepared by blending the aforesaid antibody or its salt with conventional bases for suppositories.

The composition for oral administration includes a solid or liquid dosage form, more specifically, tablets (including dragees and film-coated tablets), pills, granules, powders, capsules (including soft capsules), syrups, emulsions, suspensions, etc. Such a composition is manufactured by publicly known methods and may contain carriers, diluents or excipients conventionally used in the field of pharmaceutical preparations. As the carriers and excipients for tablets e.g., lactose, starch, sucrose and magnesium stearate are used.

Advantageously, the pharmaceutical compositions for parenteral or oral use described above are prepared into pharmaceutical preparations with a unit dose suited to fit a dose of the active ingredients. Such unit dose preparations include, for example, tablets, pills, capsules, injections (ampoules) and suppositories. The amount of the antibody contained is generally about 5 to about 500 mg per dosage unit form; it is preferred that the aforesaid antibody is contained in about 5 to about 100 mg especially in the form of injection, and in about 10 to 250 mg for the other forms.

Each of the compositions described above may further contain other active ingredients, unless any adverse interaction occurs due to blending with the antibody described above.

The dose of the preventive/therapeutic agent or diagnostic agent (pharmaceutical) comprising the antibody of the present invention may vary depending on subject to be administered, diseases to be administered, symptoms, routes for administration, etc. When used for the treatment of, e.g., obesity in an adult patient, it is advantageous that the antibody of the present invention is intravenously administered in a single dose of normally approximately 0.01 to 20 mg/kg body weight, preferably approximately 0.1 to 10 mg/kg body weight and more preferably approximately 0.1 to 5 mg/kg body weight approximately 1 to 5 times, preferably approximately 1 to 3 times a day. For other parenteral administrations (e.g., subcutaneous administration) and oral administration, the corresponding dose may be administered. When symptoms are extremely serious, the dose may be increased depending on the conditions.

In the specification of the present invention, amino acids, etc. are shown by abbreviations and in this case, they are denoted in accordance with the IUPAC-IUB Commission on Biochemical Nomenclature or by the common codes in the art, examples of which are shown below. For amino acids that may have the optical isomer, L form is presented unless otherwise indicated.

PAM: phenylacetamidomethyl
Boc: t-butyloxycarbonyl
Fmoc: 9-fluorenylmethyloxycarbonyl
Cl-Z: 2-chlorobenzyloxycarbonyl
Br-Z: 2-bromobenzyloxycarbonyl
Bzl: benzyl
Cl-Bzl: 2-chlorobenzyl
OcHex: cyclohexyl ester
OBzl: benzyl ester
Tos: p-toluenesulfonyl
HONB: N-hydroxy-5-norbornene-2,3-dicarboximido
HOBt: 1-hydroxybenzotriazole
HOOBt: 3-hydroxy-3,4-dihydro-4-oxo-1,2,3-benzotriazine
MeBzl: 4-methylbenzyl
Bom: benzyloxymethyl
Bum: t-butoxymethyl
Trt: trityl
DNP: dinitrophenyl
TFA: trifluoroacetic acid
DMF: N,N-dimethylformamide
DCM: dichloromethane
DCC: N,N'-dichlorohexylcarbodiimide
BHA: benzhydrylamine
pMBHA: p-methylbenzhydrylamine
CHO: formyl
Gly: glycine
Ala: alanine
Val: valine
Leu: leucine
Ile: isoleucine
Ser: serine
Thr: threonine
Cys: cysteine
Met: methionine
Glu: glutamic acid
Asp: aspartic acid
Lys: lysine
Arg: arginine
His: histidine
Phe: phenylalanine
Tyr: tyrosine
Trp: tryptophan
Pro: proline
Asn: asparagine
Gln: glutamine The sequence identification numbers used in the sequence listing of the specification represents the amino acid sequences of the following peptides.

[SEQ ID NO: 1]
This shows the amino acid sequence of rat GALP.

[SEQ ID NO: 2]
This shows the amino acid sequence of human GALP.

[SEQ ID NO: 3]
This shows the amino acid sequence of porcine GALP.

[SEQ ID NO: 4]
This shows the amino acid sequence of immunogen peptide (rat GALP (43-60) wherein the 43rd amino acid residue is substituted with cysteine; also represented by [$Cys^{43}$] rat GALP (43-60)).

In the hybridoma cells obtained in EXAMPLES later described, GR-1C has been deposited on International Patent Organisms Depository, National Institute of Advanced Industrial Science and Technology, located at Central 6, 1-1-1Higashi, Tsukuba, Ibaraki (postal code: 305-8566) under Accession Number FERM BP-7682 since Jul. 31, 2001.

In the anti-GALP antibody-producing hybridoma cells, GR2-1N has been deposited on International Patent Organisms Depository, National Institute of Advanced Industrial Science and Technology (formerly NIBH), located at Central 6, 1-1-1 Higashi, Tsukuba, Ibaraki (postal code: 305-8566) under Accession Number FERM BP-6682 since Mar. 17, 1999.

The antibodies acquired from the respective hybridoma cells are shown by the cell names with suffix "a."

EXAMPLES

Hereinafter, the present invention will be described in more detail, with reference to EXPERIMENTS and EXAMPLES, but they are not deemed to limit the scope of the invention.

Peptide [$Cys^{43}$] rat GALP (43-60) used in the following EXPERIMENTS and EXAMPLES was purchased from American Peptide, Co., Inc., where it was synthesized in a conventional manner.

With regard to rat GALP and porcine GALP, recombinant GALP was prepared based on the previous report (Journal of The Chemical Society-Perkin Transactions, 2000, No. 1, page-1335).

Human GALP was purchased from PHOENIX PHARMACEUTICALS, INC.

Experiment 1

Production of rat GALP (44-60)-Containing Immunogen [$Cys^{43}$] rat GALP (43-60) Represented by SEQ ID NO: 4

The complex of [$Cys^{43}$] rat GALP (43-60) and KLH was prepared and used as an immunogen.

That is, 20 mg of KLH was dissolved in 1.4 ml of 0.1 M phosphate buffer (pH 6.5). The solution was mixed with 100 µl of a DMF solution containing 2.2 mg (8 µmols) of N-(γ-maleimidobutyryloxy)succinimide (GMBS) followed by reaction at room temperature for 40 minutes. After the reaction, the mixture was fractionated on a Sephadex G-25 column and mixed with 15 mg of the maleimide-introduced KLH and 3.9 mg of [Cys$^{43}$] rat GALP (43-60). The mixture was reacted at 4° C. for 1 day. After the reaction, the mixture was dialyzed to physiological saline at 4° C. for 2 days.

Experiment 2

Immunization

BALB/C female mice of 6 to 8 weeks old was immunized with the [Cys$^{43}$] rat GALP (43-60)-KLH complex obtained in EXPERIMENT 1 by subcutaneous injection of the complex in about 60 μg/mouse, together with complete Freund's adjuvant. Subsequently, the same amount of the immunogen was boostered 2 to 3 times every 3 other weeks, together with incomplete Freund's adjuvant.

Experiment 3

Preparation of Horse Radish Peroxidase (HRP)-Labeled [Cys$^{43}$] Rat GALP (43-60)

[Cys$^{43}$] rat GALP (43-60) was crosslinked with HRP (for enzyme immunoassay, manufactured by Boehringer Mannheim) to prepare the labeled form for enzyme immunoassay (EIA). That is, 6.7 mg (168 nmols) of HRP was dissolved in 0.95 ml of 0.1M phosphate buffer (pH 6.5). The solution was mixed with 50 μl of a DMF solution containing 0.47 mg (1.65 μmols) of GMBS. After the mixture was reacted at room temperature for 30 minutes, the reaction mixture was fractionated on a Sephadex G-25 column. After 5.0 mg (117 nmols) of the maleimide-introduced HRP thus prepared was mixed with 0.74 mg (352 nmols) of [Cys$^{43}$] rat GALP (43-60), the mixture was reacted at 4° C. for a day. After the reaction, the reaction mixture was fractionated on an Ultrogel AcA44 (manufactured by LKB-Pharmacia) column to give HRP-labeled rat GALP (43-60).

Experiment 4

Assay for Antibody Titer in Antisera of Mouse Immunized with the [Cys$^{43}$] Rat GALP (43-60)-KLH Complex After boostering twice with the [Cys$^{43}$] rat GALP (43-60)-KLH complex at 3 week intervals, blood was withdrawn and collected from the fundus oculi 1 week after. The blood was centrifuged at 4° C. for 15 minutes at 12,000 rpm, the supernatant was recovered to obtain antisera. The antibody titer in the antisera was assayed by the following procedure. In order to prepare an anti-mouse immunoglobulin antibody-bound microplate, a 100 μl aliquot of 0.1M carbonate buffer (pH 9.6) containing 100 μg/ml of anti-mouse immunoglobulin antibody (IgG fraction, manufactured by CAPPEL) was dispensed in each well of a 96-well microplate, which was allowed to stand at 4° C. for 24 hours. Next, after the plate was washed with phosphate buffered saline (PBS, pH 7.4), a 300 μl aliquot of PBS containing 25% Block Ace (manufactured by Snow Brand Milk Products) was dispensed in each well and treated at 4° C. for at least 24 hours to block redundant binding sites.

After 50 μl of Buffer C (0.02M phosphate buffer, pH 7.0, containing 1% BSA, 0.4M NaCl, 0.05% 2 mM EDTA.Na (ethylenediamine-N,N,N',N'-tetraacetic acid, disodium salt, dihydrate, DOJINDO Co.) and 100 μl of antisera to the complex diluted with Buffer C were added to each well of the anti-mouse immunoglobulin antibody-bound microplate obtained, the reaction was carried out at 4° C. for 16 hours. Next, the plate was washed with PBS and 100 μl of HRP-labeled [Cys$^{43}$] rat GALP (43-60) (diluted to 300-fold with Buffer C) prepared in EXPERIMENT 3 was added thereto and the reaction was carried out at room temperature for a day. Then, the plate was washed with PBS and 100 μl of TMB Microwell Peroxidase Substrate System (KIRKEGAARD & PERRY LAB, INC., consigned to Funakoshi Co., Ltd.) was added and the reaction was carried out at room temperature for 10 minutes to assay the enzyme activity on a solid phase. By adding 100 μl of 1M phosphoric acid the reaction was terminated, and the absorption at 450 nm was measured using a plate reader (BICHROMATIC, manufactured by Dainippon Pharmaceutical Co., Ltd.).

The absorption spectra obtained are shown in FIG. 1. In FIG. 1, symbols (-◇-), (-□-), (-△-), (-○-), (-◆-), (-■-), (-▲-) and (-●-) designate mice No.1 (1a), No.2 (2a), No.3 (3a), No.4 (4a), No.5 (5a), No.6 (6a), No.7 (7a) and No.8 (8a), respectively. Symbols 1a–8a shows the antisera derived from 8 mice. From FIG. 1 it is seen that an increase of the antibody titer to [Cys$^{43}$] rat GALP (43-60) was noted in the antisera to all the complexes in 8 mice.

Example 1

Preparation of anti-[Cys$^{43}$] rat GALP (43-60) Monoclonal Antibody

Referring to FIG. 1, mice Nos. 6 and 7 producing antibodies 6a and 7a were selected as examples of screening from the antibody-producing cell lines of hybridomas from mouse immunized with the [Cys$^{43}$] rat GALP (43-60)-KLH complex.

Mice producing the antibodies 6a and 7a received the final immunization by intravenous injection of a 100–150 μg immunogen solution in 0.1 ml of physiological saline. Three or four days after the final immunization, the spleen was withdrawn from each mouse, pressed against a stainless mesh, filtered and suspended in Eagle's minimum essential medium (MEM) to give the spleen cell suspension. As cells used for cell fusion, BALB/C mouse-derived myeloma cell P3-X63.Ag8.U1(P3U1) was used (Current Topics in Microbiology and Immunology, 81, 1, 1978).

The cell fusion was performed by a modification of the original method (Nature, 256, 495, 1975). That is, the spleen cells and P3U1 were washed 3 times with serum-free MEM, respectively, and they were blended in a 5:1 proportion of the spleen cells to P3U1 in cell count. The mixture was centrifuged at 800 rpm for 15 minutes to deposit the cells. After the supernatant was thoroughly removed, the deposit was lightly unraveled and 0.3 ml of 45% polyethylene glycol (PEG) 6000 (manufactured by Kochlight) was added thereto. The mixture was allowed to stand for 7 minutes in a warm water bath of 37° C. to perform cell fusion. The fusion was followed by addition of MEM to the cells at a rate of 2 ml/min. After 15 ml of MEM in total was added, the mixture was centrifuged at 600 rpm for 15 minutes and the supernatant was removed. The cell deposit was suspended in 10% fetal calf serum-containing GIT medium (Wako Pure Chemical Industries, Ltd.) (GIT-10% FCS) in 2×10$^5$/ml of P3U1, and the suspension was plated on 192 wells of a 24-well Multidish (manufactured by Limbro) in 1 ml/well. After the plating, the cells were incubated at 37° C. in a 5% carbonic acid incubator. Twenty-four hours after, GIT-10% FCS medium (HAT medium) containing HAT (1×10$^{-4}$ M hypoxanthine, 4×10$^{-7}$ M aminopterin, 1.6×10$^{-3}$ M thymidine) was added to the cells in 1 ml/well, thereby to start HAT selective culture. The HAT selective culture was continued by discarding 1 ml of the old medium on Days 3, 6 and 9 after start of the incubation and supplementing 1 ml of HAT medium. Proliferation of the hybridoma was noted on Days 9–14 after the cell fusion. The growth of hybridomas was noted 9 to 14 days after the cell fusion. When the culture medium turned yellow (ca. 1×10$^6$ cells/ml), the supernatant was collected and the antibody titer was assayed in accordance with the procedure described in EXPERIMENT 4.

Figure 2A:
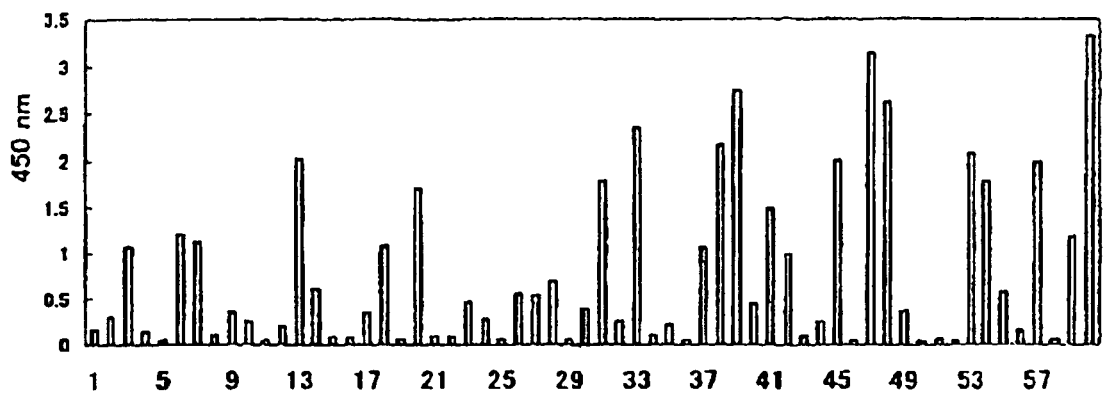
FIG. 2 shows the conditions (results of absorption spectrophotometry) that the hybridomas derived from mice immunized with the [$Cys^{43}$] rat GALP (43-60)-KLH complex produce the antibodies with the X-axis indicating the well number of the sample.
Figure 2B:
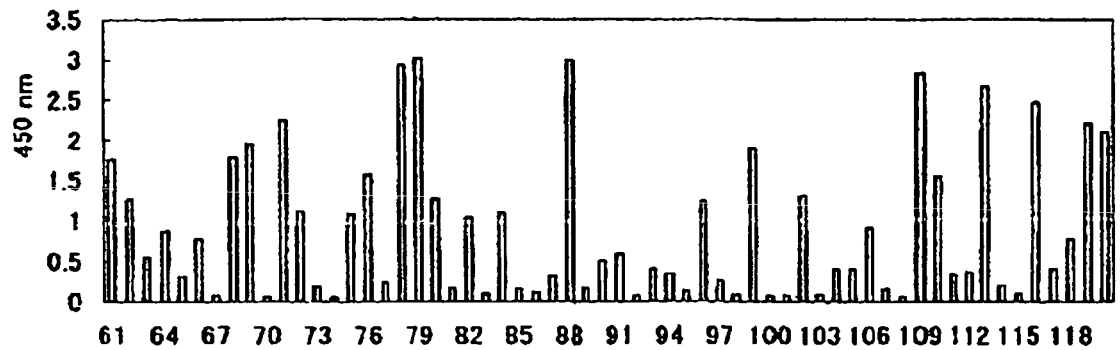
Figure 2C:
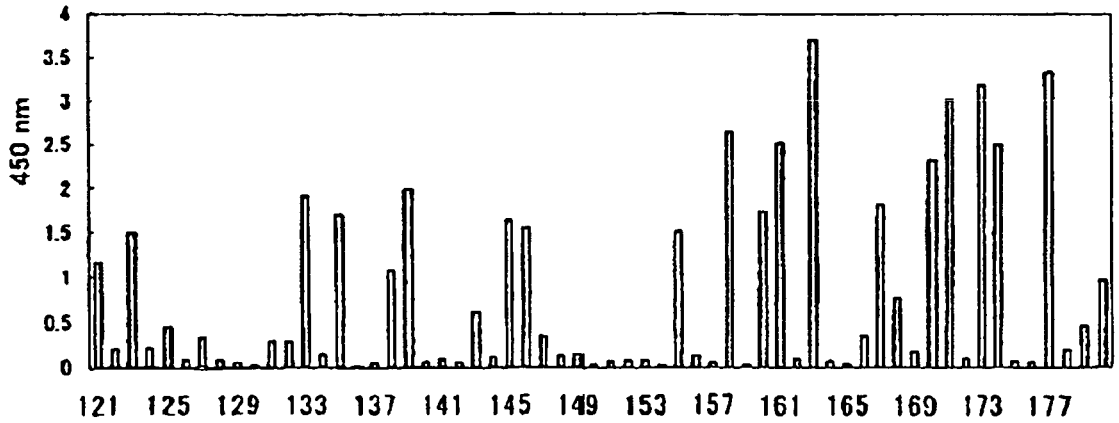

The conditions that the hybridomas derived from mice immunized with the [Cys$^{43}$] rat GALP (43-60)-KLH complex producing antibodies 6a and 7a produced the antibodies are shown in FIG. 2. From the antibody-producing hybridomas acquired, the following 5 hybridomas in total were selected (TABLE 1). Among them, hybridomas Nos. 1 and 2, which provided particularly large antibody titers (large in absorbance), were named GR-1C and GR-2C, respectively.

TABLE 1

Reactivity of monoclonal antibody[1)]

| Hybridoma No. | rat GALP | Class/Subclass | Notes |
| --- | --- | --- | --- |
| 1 | + | IgG$_{2b}$, κ | GR-1C |
| 2 | + | IgG1, κ | GR-2C |
| 3 | + | IgG1, κ | |
| 4 | ± | IgG1, κ | |
| 5 | ± | IgG1, κ | |

[1)]When 10 nM of rat GALP was present:
+: (B/B$_0$) < 0.50
±: 0.50 ≦ (B/B$_0$) < 0.80
−: 0.80 ≦ (B/B$_0$)
B: the amount of HRP-labeled rat GALP (43–60) bound to the antibody when the antigen was present
B$_0$: the amount of HRP-labeled rat GALP (43–60) bound to the antibody when no antigen was present Next, these hybridomas were cloned by limiting dilution. In cloning, thymocytes from BALB/C mice were added as feeder cells in 5×10$^5$ cells/well. After cloning, the hybridomas were intraperitoneally injected to mice (BALB/C) in 1 to 3×10$^6$ cells/mouse, to which mice 0.5 ml of mineral oil had previously been given intraperitoneally. The ascites fluid containing the antibody was collected 6 to 20 days after.

The monoclonal antibody was purified through a protein A column from the ascites fluid obtained. That is, 6 to 20 ml of the ascites fluid was diluted with an equal volume of binding buffer [1.5M glycine containing 3.5M NaCl and 0.05% NaN$_3$ (pH 9.0)], and the dilution was applied on recombinant protein A-agarose (manufactured by Seikagaku Corporation) column, which had been previously equilibrated with the binding buffer. The specific antibody was eluted with an eluting buffer [0.1M citrate buffer containing 0.05% NaN$_3$ (pH 3.0)]. The eluate was dialyzed to PBS at 4° C. for 2 days, which was subjected to cell-free filtration through a filter of 0.22 μm (manufactured by Millipore) and then stored at 4° C. or −80° C.

In class/subclass determinations of the monoclonal antibodies, enzyme-linked immunosorbent assay (ELISA) using purified monoclonal antibody-bound solid phase was carried out. That is, 100 μl each of 0.1M carbonate buffer (pH 9.6) solution containing 2 μg/ml of the antibody was dispensed on a 96-well microplate, which was allowed to stand at 4° C. for 24 hours. Following the procedure described in EXPERIMENT 4, redundant binding sites in the wells were blocked with Block Ace. Thereafter, the class and subclass of immobilized antibodies were determined by ELISA using an isotyping kit (Mouse-Typer™ Sub-Isotyping Kit, manufactured by Biorad).

Example 2

Competitive Enzyme Immunoassay (Competitive Method—EIA)

The monoclonal antibodies were prepared using the [Cys$^{43}$] rat GALP (43-60)-KLH complex as an immunogen and their reaction specificity was examined by the following method.

First, the antibody titers of the respective solutions of monoclonal antibodies GR-1Ca and GR-2Ca were assayed by the method described in EXPERIMENT 4, and the antibody level wherein the binding amount of a labeled form reached about 50% of the saturation binding amount was determined as an antibody level used for competitive assay-EIA. Next, 50 μl of a rat GALP, human GALP or porcine GALP solution, which was diluted with Buffer C in a concentration of 10$^{-6}$ M-10$^{-10}$ M, was added to each well of the anti-mouse immunoglobulin antibody-bound microplate described in EXPERIMENT 4, to which well (i) 50 μl of the anti-[Cys$^{43}$] rat GALP (43-60) antibody GR-1 Ca solution or GR-2Ca solution diluted with Buffer C to have 80 ng/ml and (ii) 50 μl of the HRP-labeled [Cys$^{43}$] rat GALP (43-60) diluted to 400-fold with Buffer C described in EXPERIMENT 3 had been added, followed by reaction at 4° C. for 16 hours. After the reaction, the plate was washed with PBS and the enzyme activity on the anti-mouse immunoglobulin antibody-bound microplate was assayed by the method described in EXPERIMENT 4.

Figure 3:
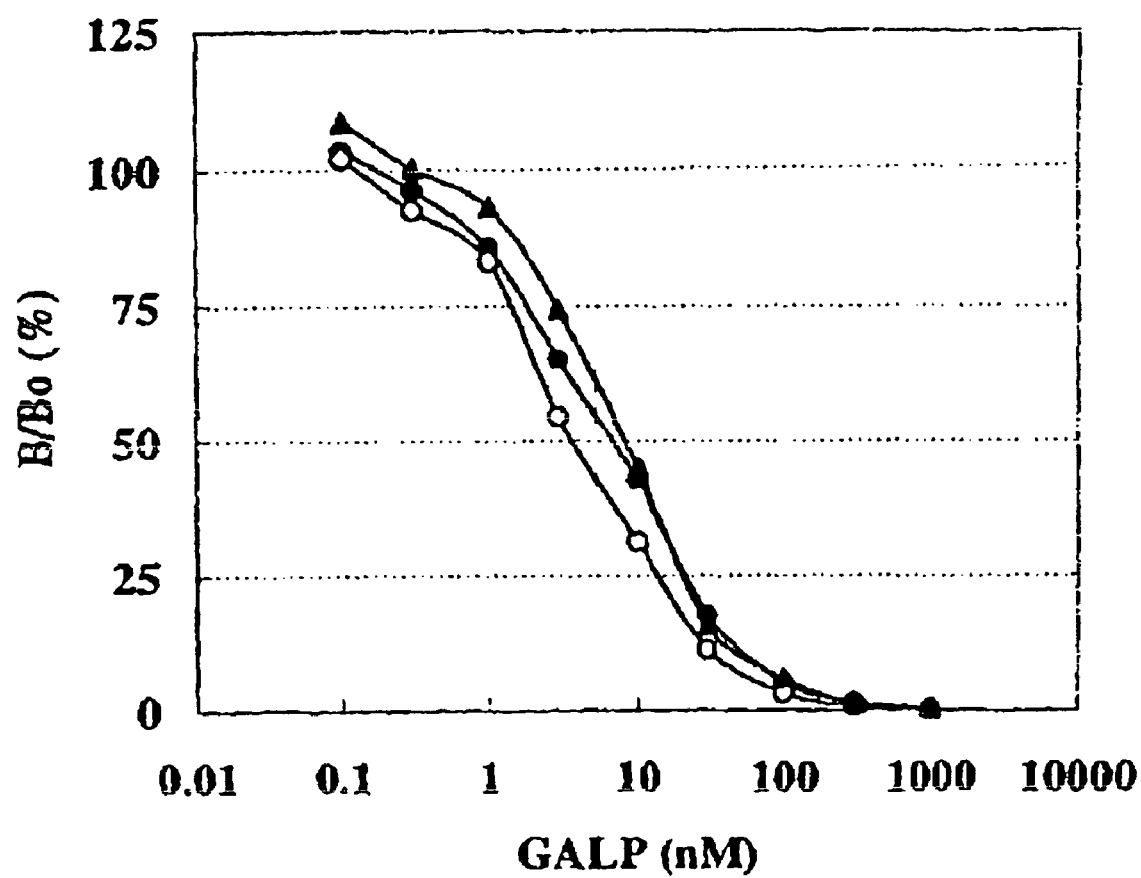
FIG. 3 shows the results of GR-1 Ca by the competitive method-EIA.
Figure 4:
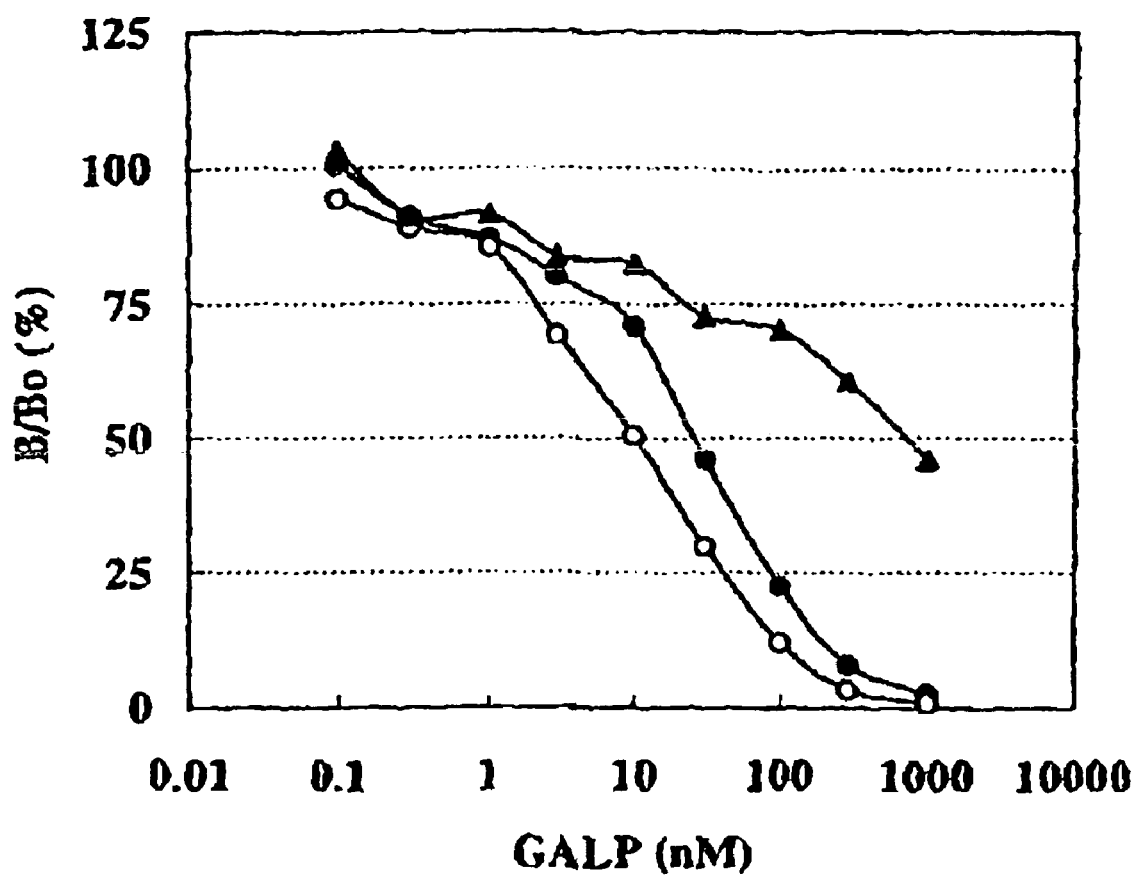
FIG. 4 shows the results of GR-2Ca by the competitive method-EIA.

The results with GR-1Ca and GR-2Ca by the competitive method are shown in FIGS. 3 and 4, respectively.

In FIGS. 3 and 4, symbols (-●-), (-○-) and (-●-) designate the reaction to human GALP, rat GALP and porcine GALP, respectively. It is noted from the results that both antibodies have the reactivities with rat GALP, human GALP and porcine GALP.

From the standard curve of GR-1Ca it was made clear that the GALP level giving (B/B$_0$)=0.5 was rat GALP: 3 nM, human GALP: 7 nM and porcine GALP: 8 nM (FIG. 3). These results suggest that GR-1Ca would show nearly equal high reactivities with any of rat, human and porcine types.

Furthermore, the standard curve of GR-2Ca indicates that the GALP level providing (B/B$_0$)=0.5 was rat GALP: 10 nM, human GALP: 20 nM and porcine GALP: 500 nM (FIG. 4). These results suggest that the reactivity of GR-2Ca with porcine GALP would be low, though the reactivities with rat GALP and human GALP were nearly equal.

Experiment 5

Preparation of HRP-Labeled Anti-GALP Monoclonal Antibody (GR2–1Na-HRP)

After 50 μl of DMF containing 0.74 μmol of GMBS was added to 0.1M phosphate buffer (pH 6.8) containing 9.25 mg (61.7 μmols) of the purified fraction of the monoclonal antibody GR2–1N, which recognized the N-terminal region (1–9) of GALP described in Published Japanese Patent Application KOKAI No. 2000-157273, the mixture was reacted at room temperature for 40 minutes. The reaction solution was applied on a Sephadex G-25 column (eluant, 0.1M phosphate buffer, pH 6.7) for separation to give 7.17 mg of the maleimide-introduced antibody fraction. Next, 60 μl of DMF containing 6.67 μmols of N-succinimidyl-3-(2-pyrimidyldithio)propionate (SPDP) was added to 1.4 ml of 0.02M phosphate buffer (also containing 0.15M NaCl) (pH 6.8) containing 17.8 mg (445 μmols) of HRP, followed by reaction at room temperature for 40 minutes. Subsequently, 0.4 ml of 0.1M acetate buffer (pH 4.5) containing 66 μmols of dithiothreitol was added. After reacting at room temperature for 20 minutes, the reaction mixture was applied on a Sephadex G-25 column (eluant, 0.1M phosphate buffer, pH 6.0, containing 2 mM EDTA) for separation to give 9.8 mg of SH-introduced HRP. Next, 8 mg of the SH-introduced HRP was mixed with 3 mg of the maleimide-introduced antibody fraction. After the mixture was concentrated to about 0.5 ml with Collodion Bag (manufactured by Sartorius K. K.), the concentrate was allowed to stand at 4° C. for 16 hours. The reaction solution was applied on Sephacryl S-300HR column (manufactured by Pharmacia) using 0.1 M phosphate buffer, pH 6.5, as an eluant. Thus, the GR2-1Na-HRP complex fraction was purified.

Example 3

Sandwich Assay—EIA (Specificity and Sensitivity of the Sandwich Assay—EIA)

After 100 µl each of 0.1M carbonate buffer (pH 9.6 solution) containing 15 µg/ml of the purified monoclonal antibody GR-1Ca obtained in EXAMPLE 1 was dispensed in a 96-well microplate, the plate was allowed to stand at 4° C. for 24 hours. The redundant binding sites in the wells were inactivated by adding 400 µl of Block Ace diluted with PBS to 4-fold.

To the plate prepared as described above, 100 µl each of rat GALP, human GALP and porcine GALP, diluted with Buffer C, was added, followed by reaction at 4° C. for 24 hours. After washing with PBS, the enzyme activity on the solid phase was assayed by the method described in EXPERIMENT 4 using TMB (enzyme reaction for 20 minutes).

Figure 5:
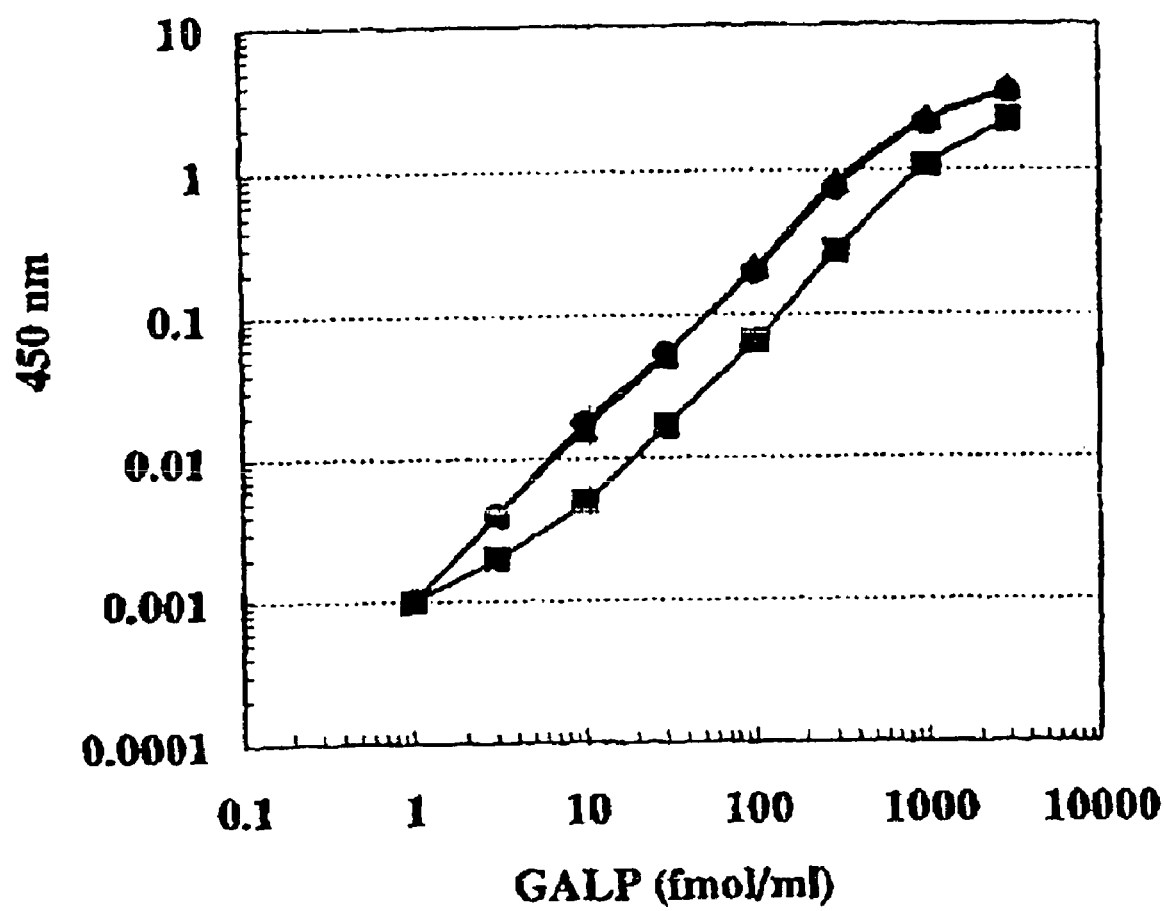
FIG. 5 shows the assay results of GR-1Ca by the sandwich method-EIA.

The results are shown in FIG. 5.

In FIG. 5, symbols (-●-), (-■-) and (-▲-) designate absorptions of rat GALP, human GALP and porcine GALP, respectively. FIG. 5 revealed that rat GALP, human GALP and porcine GALP could be detected by the sandwich method-EIA with an extremely high sensitivity.

That is, the sandwich assay-EIA enables to detect rat GALP, human GALP and porcine GALP in 0.3 fmol/well.

It was thus found that by way of illustration, the sandwich assay-EIA using GR-1Ca as a solid phase and GR-1Na-HRP as a marker can selectively detect human metastin with an extremely high sensitivity.

Example 4

Quantification of Rat GALP in Plasma

Rat plasma was diluted to 2-fold with an equal volume of Buffer EC (0.1M phosphate buffer, pH 7.0, containing 0.2% BSA, 0.4M NaCl, 2 mM EDTA.Na, 10% Block Ace, 0.05% CHAPS and 0.05% sodium azide). Rat GALP was then quantified by the sandwich method-EIA in EXAMPLE 3 described above.

The results are shown in TABLE 2.

TABLE 2

| | Immunoreactivity of rat GALP | |
|---|---|---|
| No. | Male (fmol/ml) | Female (fmol/ml) |
| 1 | 10.8 | 14.3 |
| 2 | 9.40 | 7.22 |
| 3 | 6.61 | 6.05 |
| 4 | 20.5 | 6.34 |
| 5 | 3.43 | 7.51 |

TABLE 2-continued

| | Immunoreactivity of rat GALP | |
|---|---|---|
| No. | Male (fmol/ml) | Female (fmol/ml) |
| 6 | 7.24 | 16.5 |
| 7 | 11.3 | 7.22 |
| 8 | 5.83 | 14.9 |
| 9 | 6.94 | 8.38 |
| 10 | 7.78 | 8.38 |
| 11 | | 5.46 |

In rat plasma (1 ml), rat GALP was present in:
Male: 8.98 ± 1.48 fmol/ml (mean ± SEM, n = 10)
Female: 9.30 ± 1.19 fmol/ml (mean ± SEM, n = 11)

Example 5

Fraction of GALP in Rat Plasma by Reverse Phase High Performance Liquid Chromatography (RP-HPLC)

To identify the immunological activity of GALP contained in rat plasma, which was described in EXAMPLE 4, 24 ml of acetonitrile was added to and mixed with 12 ml of rat plasma. The mixture was centrifuged to remove proteins. After the supernatant was lyophilized, this fraction was concentrated followed by fractionation on reverse phase HPLC using ODS-80™.

Column conditions:

Column: ODS-80™ (4.6×250 mm)

Eluants: Eluant A (5% acetonitrile containing 0.05% trifluoroacetic acid) Eluant B (60% acetonitrile containing 0.05% trifluoroacetic acid)

Elution method: The acetonitrile concentration was increased from 5% to 30% for the initial 5 minutes and then linearly increased to 30–50% over 30 minutes.

Flow rate: 1.0 ml/min.

Fractionation: 0.5 ml/tube

After the eluted fraction was lyophilized, the lyophilized product was dissolved in 250 µl of Buffer C and the solution was provided for the sandwich method-EIA described in EXAMPLE 3.

Figure 6:
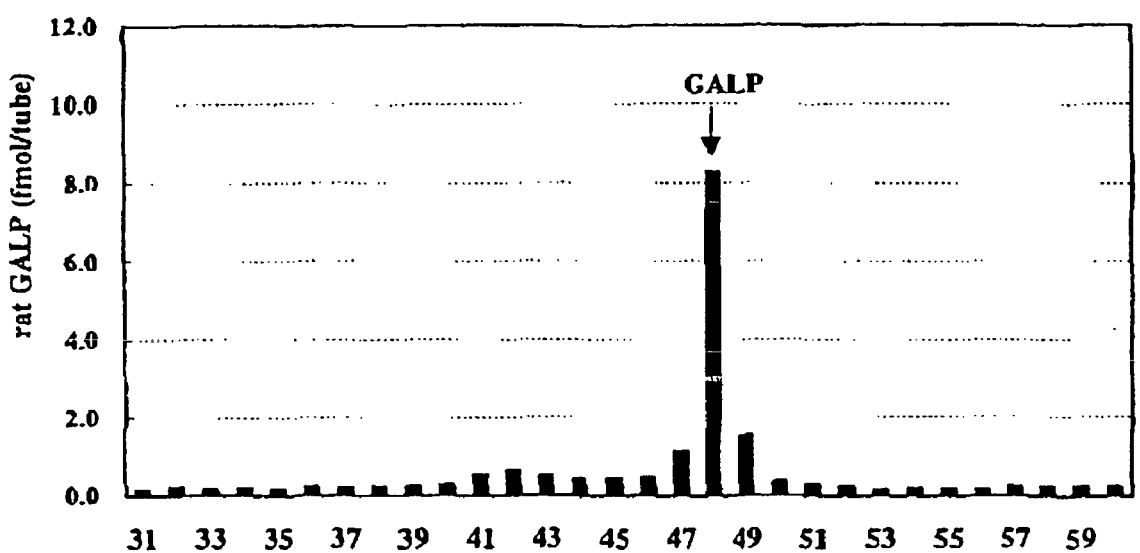
FIG. 6 shows the assay results of rat plasma by the sandwich method-EIA with the X-axis indicating the fraction number of the sample.

The results are shown in FIG. 6.

The immunological activity of rat GALP in plasma was detected almost at the eluted position of rat GALP. Thus, it was confirmed that the sandwich method-EIA detected rat GALP

Example 6

Quantification of Human GALP in Plasma

Human plasma was diluted to 2-fold with an equal volume of Buffer EC [0.1M phosphate buffer, pH 7.0, containing 0.2% BSA, 0.4M NaCl, 2 mM EDTA.Na, 10% Block Ace, 0.05% CHAPS and 0.05% sodium azide]. Human GALP in human plasma was then quantified by the sandwich method-EIA in EXAMPLE 3 described above. The human plasma was provided from healthy volunteers of Takeda Chemical Industries, Ltd., giving the informed consent.

The results are shown in TABLE 3.

TABLE 3

Immunoreactivity of human GALP

| No. | Male (fmol/ml) | Female (fmol/ml) |
| --- | --- | --- |
| 1 | 30.9 | 33.7 |
| 2 | 28.3 | 204 |
| 3 | 7.41 | 15.1 |
| 4 | 29.3 | 52.7 |
| 5 | 10.9 | 180.5 |
| 6 | 8.90 | 55.2 |
| 7 | 161.3 | 56.4 |
| 8 | 55.2 | |
| 9 | 28.8 | |
| 10 | 82.2 | |
| 11 | 273.5 | |
| 12 | 67.1 | |
| 13 | 11.9 | |
| 14 | 136.7 | |
| 15 | 398.2 | |
| 16 | 15.4 | |

In human plasma (1 ml), human GALP was present in:
Male: 84.1 ± 25.6 fmol/ml (mean ± SEM, n = 18)
Female: 75.5 ± 25.5 fmol/ml (mean ± SEM, n = 7)

It is seen from the results that this assay system becomes an important means for investigating changes of GALP in plasma.

Example 7

Quantification of GALP in Chronic Inflammation Model or Rat with Adjuvant-induced Arthritis Male Lewis rats (7 weeks old, Charles River Japan, Inc.) were intracutaneously injected for sensitization with 250 μg of killed Mycobacterium tuberculosis (H37 RA, Difco), which was suspended in 0.05 ml of liquid paraffin, at the left hind limb (group A.A.). The vehicle group received 0.05 ml of liquid paraffin. The experiments were all conducted in 7 rats. The limb volume of adjuvant-sensitized rats at the hind limb with no injection of the adjuvant (right hind limb) and the limb volume of the non-sensitized rats at the right hind limb were measure prior to injection and on day 14 after the injection. Rats were decapitated 24 hours and 14 days after the injection. Plasma was prepared from the blood collected. After the rat plasma was diluted to 2-fold with an equal volume of Buffer EC [0.1M phosphate buffer, pH 7.0, containing 0.2% BSA, 0.4M NaCl, 2 mM EDTA.Na, 10% Block Ace, 0.05% CHAPS and 0.05% sodium azide], rat GALP was quantified by the sandwich method-EIA described in EXAMPLE 3.

The GALP levels in blood are shown below.

The GALP levels showed 24 hours after adjuvant sensitization; vehicle group: 10.1±3.1 fmols/ml and group A.A.: 4.5±0.6 fmols/ml; and 14 days after the adjuvant sensitization; vehicle group: 15.1±3.5 fmols/ml and group A.A.: 3.4±0.4 fmols/ml. In both of 24 hours after and 14 days after the adjuvant sensitization, the GALP level in blood significantly decreased as compared to the vehicle group (p<0.05).

From the results it is noted that GALP could be a marker of adjuvant-induced arthritis. Furthermore, it is noted that the GALP in blood was consumed by onset of arthritis.

Also, the hypophysis was removed, boiled for 10 minutes in 5 ml of distilled water and then cooled in ice water. Acetic acid and pepstatin (Peptide Institute, Inc.) were added to the mixture in final concentrations of 1M and 10 μg/ml, respectively. The hypophysis was homogenized using a homogenizer. Then, the protein level in the solution was determined with Protein Assay Kit (Biorad). The hypophysis homogenate solution was centrifuged at 12,000 rpm for 30 minutes. The supernatant was concentrated/pre-treated using 265 mg of Sep-Pak Plus C18 cartridge (Waters, Inc.), and rat GALP was quantified by the sandwich-EIA described in EXAMPLE 3 above. The pre-treatment of the hypophysis extract was as follows. The hypophysis extract added with 2 ml of 4% acetic acid was loaded on Sep-Pak Plus C18 cartridge activated by sequentially passing through the cartridge 5 ml of methanol and 5 ml of 0.1% TFA-containing distilled water. After the addition, the cartridge was washed with 5 ml of 0.1% TFA-containing distilled water and eluted with 3 ml of 0.1% TFA-containing 60% acetonitrile, followed by lyophilization. The concentrated fraction was reconstituted in 0.25 ml of Buffer EC and provided for quantification by the sandwich method-EIA of EXAMPLE 3 described above.

The GALP contents in the hypophysis are shown below:

24 hours after adjuvant sensitization; vehicle group: 3.1±0.3 fmols/ml and group A.A.: 4.9±0.7 fmols/ml; and 14 days after the adjuvant sensitization; vehicle group: 1.6±0.2 fmols/ml and group A.A.: 2.8±0.3 fmols/ml. In both of 24 hours after and 14 days after the adjuvant sensitization, the GALP contents in the hypophysis significantly increased as compared to the vehicle group (p<0.01).

From the results it is noted that the production of GALP was promoted for the purpose of preventing the onset of arthritis.

Example 8

Quantification of GALP in Lipopolysaccharide-received Rat

Male Wistat rats (8 weeks old, Charles River Japan, Inc.) were intraperitoneously injected with lipopolysaccharide (LPS) (Wako Pure Chemical Industries, Ltd.) dissolved in physiological saline in doses of 1 m 3 and 10 mg/kg (LPS group, n=5–7). The vehicle group (n=8) received 1 ml/kg of physiological saline. Rats were decapitated 12 hours after the injection for blood collection. Plasma was prepared from the collected blood. After the plasma was diluted to 2-fold with an equal volume of Buffer EC [0.1M phosphate buffer, pH 7.0, containing 0.2% BSA, 0.4 M NaCl, 2 mM EDTA.Na, 10% Block Ace, 0.05% CHAPS and 0.05% sodium azide], rat GALP was quantified by the sandwich method-EIA described in EXAMPLE 3.

Figure 7:
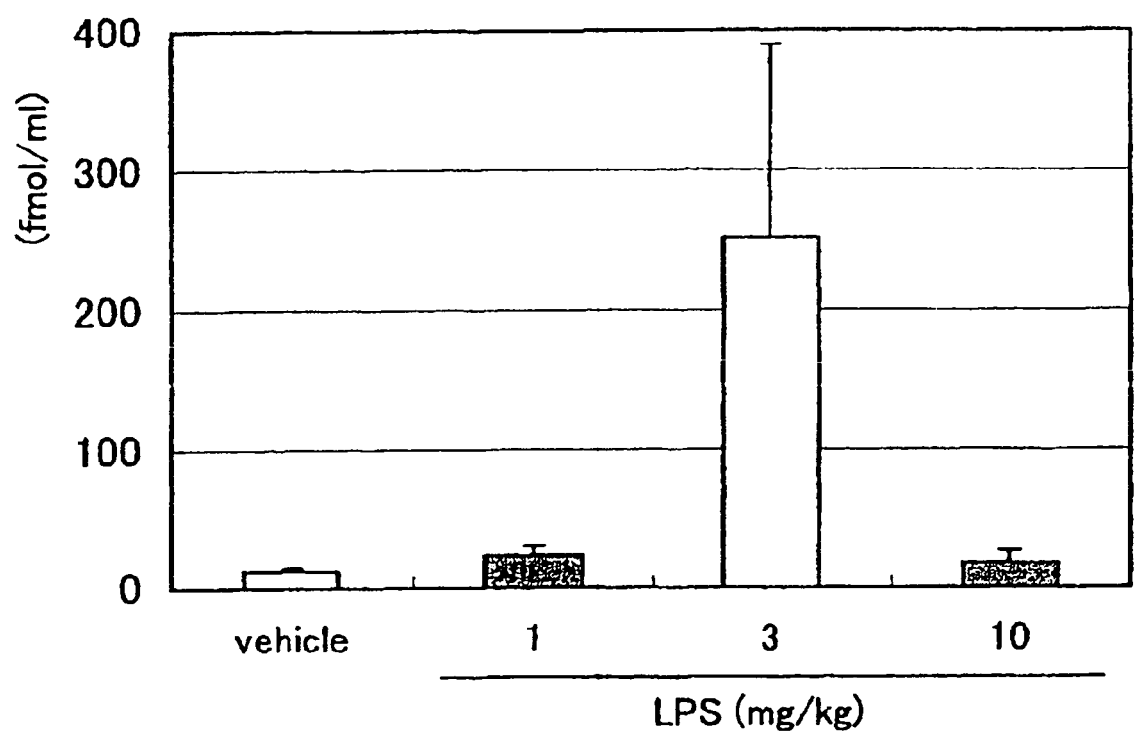
FIG. 7 shows the assay results in EXAMPLE 8 by the sandwich method-EIA, wherein the value on the ordinate indicates a mean value±standard error.

The GALP levels in blood are shown in FIG. 7.

The LPS group administered with 3 mg/kg showed the highest level (251±181 fmols/ml), which was not significant but higher as compared to the vehicle group (12.0±2.0 fmols/ml).

Furthermore, the hypophysis was removed and the GALP level in the hypophysis was measured in a manner similar to EXAMPLE 7 described above.

Figure 8:
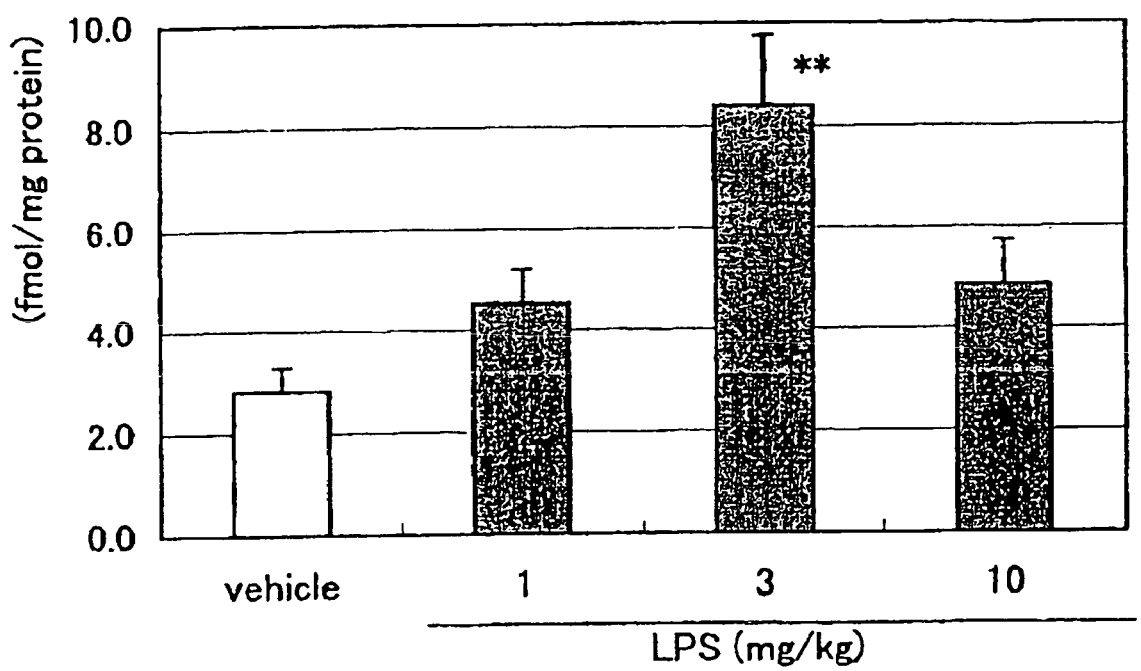
FIG. 8 shows the assay results in EXAMPLE 8 by the sandwich method-EIA, wherein the value on the ordinate indicates a mean value±standard error. :$p<=0.01$

The results are shown in FIG. 8.

As observed with the GALP level in blood, the LPS group administered with 3 mg/kg showed the highest level (8.39±1.37 fmols/mg protein), which was significantly higher than the vehicle group (2.82±0.48 fmols/mg protein) (p<0.01).

The results reveal that GALP is a factor that its production is enhanced by stimulation of endotoxins, as in cytokines. GALP is considered to be a factor associated with regulation of the production of cytokines

Example 9

Quantification of the Hypophysis GALP Level Under Load Deprived of Water

Male Wistat rats (8 weeks old, Charles River Japan, Inc.) were deprived of water and fed for 2, 4 and 7 days. After decapitation, the posterior lobe of hypophysis was withdrawn and collected. The GALP levels in the hypophysis were determined as in EXAMPLE 7 described above.

Figure 9:
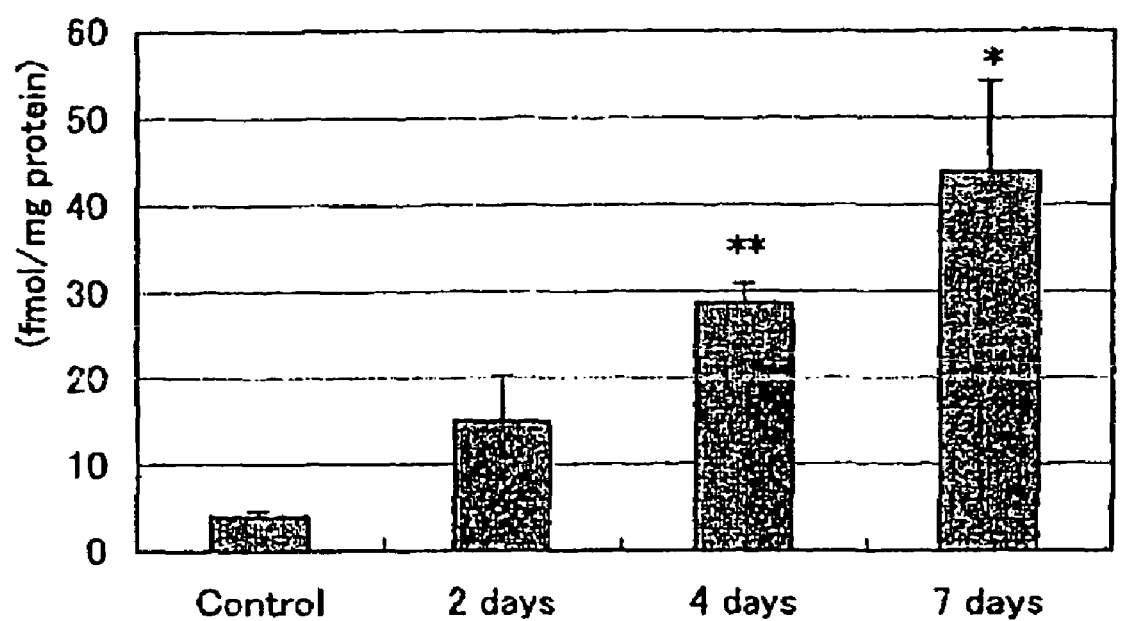
FIG. 9 shows the assay results in EXAMPLE 9 by the sandwich method-EIA, wherein the value on the ordinate indicates a mean value±standard error. : $p<=0.01$

The results are shown in FIG. 9.

The GALP levels significantly increased on day 4 (28.7±2.29 fmols/mg protein) and day 7 (43.8±10.7 fmols/mg protein) when deprived of water, as compared to the group with free access to water (3.93±0.75 fmols/mg protein).

The results reveal that changes of the GALP level in the organs can also be assayed with a high sensitivity, using the antibody of the present invention. It is also noted that GALP is a factor which participates in regulating water and osmotic pressure in vivo.

INDUSTRIAL APPLICABILITY

The antibody of the present invention is useful in developing a therapeutic, preventive and diagnostic agent for diseases associated with GALP or its derivatives. By using hybridoma cells containing the antibody of the present invention, the antibody of the present invention can be produced in an industrial scale. Furthermore, pharmaceuticals (especially diagnostic products) comprising the antibody of the present invention are useful for diagnosis of diseases/symptoms associated with GALP or its derivatives [for example, insufficient LH secretion-related diseases (e.g., obesity, sterility, irregular menstruation, dysmenorrhea, amenorrhea, premenstrual syndrome, menopausal symptoms, dyspituitarism, etc.), LH oversecretion-related disorders (e.g., prostate cancer, prostatic hyperplasia, endometriosis, precocious puberty, ovarian cancer, LH-producing pituitary tumor, etc.), dementia, diabetes, immune disorders [e.g., collagen diseases (e.g., systemic lupus erythematosus, scleroderma (systemic scleroderma), dermatomyositis, chronic articular rheumatism, rheumatic fever, periarteritis nodosa, etc.), rheumatic disorders (e.g., arthritis deformans, traumatic arthritis, gout, pseudogout, ulcerative colitis, hemophilia), inflammation, myasthenia gravis, glomerulonephritis, multiple sclerosis, Sjögren's syndrome, insulin-resistant diabetes, etc.], abnormalities in water-electrolyte metabolism (e.g., pollakiuria, hyponatremia, hypernatremia, hypokalemia, hyperkalemia, metabolic alkalosis, etc.) or the like] and so on. Also by using the antibody of the present invention, the level of GALP or its derivatives can be assayed with a high sensitivity. Thus, the quantification method of the present invention is useful for diagnosis, prevention or treatment of diseases/conditions associated with GALP or its derivatives [for example, insufficient LH secretion-related diseases (e.g., obesity, sterility, irregular menstruation, dysmenorrhea, amenorrhea, premenstrual syndrome, menopausal symptoms, dyspituitarism, etc.), LH oversecretion-related disorders (e.g., prostate cancer, prostatic hyperplasia, endometriosis, precocious puberty, ovarian cancer, LH-producing pituitary tumor, etc.), dementia, diabetes, immune disorders [e.g., collagen diseases (e.g., systemic lupus erythematosus, scleroderma (systemic scleroderma), dermatomyositis, chronic articular rheumatism, rheumatic fever, periarteritis nodosa, etc.), rheumatic disorders (e.g., arthritis deformans, traumatic arthritis, gout, pseudogout, ulcerative colitis, hemophilia), inflammation, myasthenia gravis, glomerulonephritis, multiple sclerosis, Sjögren's syndrome, insulin-resistant diabetes, etc.], abnormalities in water-electrolyte metabolism (e.g., pollakiuria, hyponatremia, hypernatremia, hypokalemia, hyperkalemia, metabolic alkalosis, etc.) or the like] and so on.

The invention claimed is:

1. An isolated antibody specifically reacting with the partial peptide in the C-terminal region consisting of the 44th–53rd amino acid sequence in the amino acid sequence represented by SEQ ID NO:2.

2. The antibody according to claim 1, which is labeled.

3. The antibody according to claim 1, which is a monoclonal antibody.

4. A monoclonal antibody, which is GR-1Ca produced by a hybridoma cell GR-1C (FERM BP-7682).

5. A hybridoma cell, which produces the monoclonal antibody of claim 3.

6. A hybridoma cell, which is GR-1C (FERM BP-7682).

7. A composition comprising the antibody according to claim 1, and a pharmaceutically acceptable carrier.

8. A diagnostic product comprising an isolated antibody specifically reacting with the partial peptide in the C-terminal region consisting of the 44th–53rd amino acid sequence in the amino acid sequence represented by SEQ ID NO: 2.

* * * * *

```
                        SEQUENCE LISTING

<160> NUMBER OF SEQ ID NOS: 4

<210> SEQ ID NO 1
<211> LENGTH: 60
<212> TYPE: PRT
<213> ORGANISM: Rat

<400> SEQUENCE: 1

Ala Pro Ala His Arg Gly Arg Gly Gly Trp Thr Leu Asn Ser Ala Gly
 1               5                  10                  15

Tyr Leu Leu Gly Pro Val Leu His Leu Ser Ser Lys Ala Asn Gln Gly
            20                  25                  30

Arg Lys Thr Asp Ser Ala Leu Glu Ile Leu Asp Leu Trp Lys Ala Ile
        35                  40                  45

Asp Gly Leu Pro Tyr Ser Arg Ser Pro Arg Met Thr
    50                  55                  60

<210> SEQ ID NO 2
<211> LENGTH: 60
<212> TYPE: PRT
<213> ORGANISM: Human

<400> SEQUENCE: 2
```

```
Ala Pro Ala His Arg Gly Arg Gly Gly Trp Thr Leu Asn Ser Ala Gly
 1               5                  10                  15

Tyr Leu Leu Gly Pro Val Leu His Leu Pro Gln Met Gly Asp Gln Asp
            20                  25                  30

Gly Lys Arg Glu Thr Ala Leu Glu Ile Leu Asp Leu Trp Lys Ala Ile
        35                  40                  45

Asp Gly Leu Pro Tyr Ser His Pro Pro Gln Pro Ser
        50                  55                  60

<210> SEQ ID NO 3
<211> LENGTH: 60
<212> TYPE: PRT
<213> ORGANISM: Porcine

<400> SEQUENCE: 3

Ala Pro Val His Arg Gly Arg Gly Gly Trp Thr Leu Asn Ser Ala Gly
 1               5                  10                  15

Tyr Leu Leu Gly Pro Val Leu His Pro Pro Ser Arg Ala Glu Gly Gly
            20                  25                  30

Gly Lys Gly Lys Thr Ala Leu Gly Ile Leu Asp Leu Trp Lys Ala Ile
        35                  40                  45

Asp Gly Leu Pro Tyr Pro Gln Ser Gln Leu Ala Ser
        50                  55                  60

<210> SEQ ID NO 4
<211> LENGTH: 18
<212> TYPE: PRT
<213> ORGANISM: Rat

<400> SEQUENCE: 4

Cys Leu Trp Lys Ala Ile Asp Gly Leu Pro Tyr Ser Arg Ser Pro Arg
 1               5                  10                  15

Met Thr
```